United States Patent [19]
Klug

[11] Patent Number: 5,962,242
[45] Date of Patent: Oct. 5, 1999

[54] METHODS OF PREDICTING ESTROGEN-DEPENDENT OSTEOPENIA

[75] Inventor: Thomas L. Klug, Tampa, Fla.

[73] Assignee: Immuna Care Corporation, Bethlehem, Pa.

[21] Appl. No.: 08/917,650

[22] Filed: Aug. 22, 1997

Related U.S. Application Data

[63] Continuation-in-part of application No. 08/715,406, Sep. 18, 1996, Pat. No. 5,854,009
[60] Provisional application No. 60/003,966, Sep. 19, 1995.
[51] Int. Cl.$^6$ .......................... G01N 33/53; G01N 33/483; G01N 33/50; G01N 33/532
[52] U.S. Cl. ..................... 435/7.93; 435/7.1; 435/7.9; 435/7.92; 435/7.93; 435/40.52; 436/543; 436/544; 436/545; 436/546
[58] Field of Search ............................ 435/7.1, 7.9, 7.92, 435/7.93, 40.52; 436/543, 544, 545, 546

[56] References Cited

FOREIGN PATENT DOCUMENTS 409176 1/1991 European Pat. Off. .

OTHER PUBLICATIONS

Arcos et al. (1967) Biochemistry 6:2032–9.
Bradlow et al. (1995) Ann. N.Y. Acad. Sci. 768:180,198.
Bradlow et al. (1985) Proc. Natl. Acad. Sci. USA 82:6295–9.
Emons et al. (1979) Acta Endocr., Copenh. 91:158–66.
Fishman et al. (1984) J. Steroid Biochem. 20:1077–81.
Fishman et al. (1980) Proc. Natl. Acad. Sci. USA 77:4957–60.
Galbraith et al. (1989) N. Engl. J. Med. 321:269–74.
Hellman et al. (1971) J. Clin. Endocrinol Metab. 33:138–44.
Hodge et al, 1995, J Bone Miner Res 10(Suppl 1):S444.
Holzman, D. (1995) J. Natl. Can. Inst. 87:1207–9.
Ikegawa et al. (1983) J. Steroid Biochem. 18:329–32.
Ikegawa et al. (1982) Steroids 39:557–67.
Klug et al. (1994) Steroids 59:648–55.
Lim et al, 1997, J Clin Endocrinol Metab, 82:1001–6.
Lindner et al. (1981) J. Steroid Biochem 15:131–6.
Magini et al, 1990, J Steroid Biochem, 36:523–6.
Mattox et al. (1979) J. Steroid Biochem. 10:167–72.
Michnovicz et al. (1990) Steroids 55:22–6.
Michnovicz et al. (1988) Steroids 52:69–83.
Newfield et al. (1993) Anticancer Res. 13:337–42.
Nilas et al, 1988, Bone Miner, 4:95–103.
Pazzagli et al. (1987) J. Steroid Biochem. 27:399–404.
Rader et al. (1973) Am. J. Obstet. Gynecol. 116:1069–73.
Samarajeewa et al. (1980) Steroids 36:611–8.
Schneider et al. (1982) Proc. Natl. Acad. Sci. USA 79:3047–51.
Sepkovic et al. (1995) Ann. N.Y. Acad. Sci. 768:312–6.
Yoshizawa et al. (1971) J. Clin. Endocrinol. 32:3–6.
Zumhoff et al. (1968) J. Clin. Endocrinol 28:937–41.
Zumhoff et al. (1966) J. Clin. Endocrinol Metab. 26:960–6.

*Primary Examiner*—Paula K. Hutzell
*Assistant Examiner*—Geetha P. Bansal
*Attorney, Agent, or Firm*—Klauber & Jackson

[57] ABSTRACT

Diagnostic/prognostic methods are provided for screening for pathologies wherein an alteration in estrogen metabolism is indicative of a pathology or a susceptibility thereto which comprise detecting and/or quantifying directly in tissues and body fluids of mammals abnormal levels of estrone metabolites and their glucuronide conjugates. Particularly preferred methods involve the use of the 16OHE1-glucuronide fraction, i.e., the fraction which contains 16α-hydroxyestrone (16OHE1) and its conjugates, 16OHE1-3-glucuronide. Methods of preparing reagents to detect said 16OHE1-glucuronide fraction in tissues and body fluids are disclosed as well as test kits for performing the disclosed assays.

44 Claims, 6 Drawing Sheets

METHODS OF PREDICTING ESTROGEN-DEPENDENT OSTEOPENIA

This Application is a continuation-in-part of co-pending U.S. patent application Ser. No. 08/715,406, filed Sep. 18, 1996. This application claims benefit of Provisional Application 60/003,966, filed Sep. 19, 1995.

FIELD OF INVENTION

This invention relates to the medical arts, and more specifically, to the area of diagnostics/prognostics, particularly for assessing the impact of estrogen on bone mineral metabolism, and predicting bone mineral density and changes in bone mineral density utilizing methods for detection of endogenous estrogens. The present invention thus relates to the use of estrogen metabolites, and especially to the estrogen metabolites, 2-hydroxyestrone, (2OHE1; 1,3,5 [10]estratrien-2,3-diol-17-one) and 2-methoxyestrone (2MeoE1; 1,3,5[10]estratrien-2,3-diol-17-one 2-methyl ether), 16α-hydroxyestrone (16OHE1; 1,3,5[10]estratrien-3,16α-diol-17-one), as well as conjugates thereof, and assays designed to detect and/or quantify these metabolites in body fluids of mammals. Particularly preferred metabolites for measurement are 2OHE1, 2MeoE1, 16OHE1 and its 3-D-glucopyranosiduronic acid ethers (3-glucuronides), and especially, the 2OHE1-, 2MeoE1-, and 16OHE1-3-glucuronides.

BACKGROUND OF THE INVENTION

Osteoporosis is a systemic skeletal disease characterized by low bone mass and microarchitectural deterioration of bone tissue, with a consequent increase in bone fragility and susceptibility to fracture. Although age-related bone loss occurs in both men and women, it begins earlier, and progresses more rapidly, in women. In the third or fourth decade of a woman's life, bone mass begins to decline because of an imbalance between the volume of mineral and matrix removed and that reincorporated during the bone remodeling process. When menopause occurs, the rate of bone loss accelerates and is particularly rapid in the first postmenopausal decade. This accelerated bone loss is caused by estrogen deficiency, which not only induces an enhanced, focal imbalance at remodeling sites but also increases the overall rate of remodeling. Riggs and Melton have written extensively on this topic, and have described two distinct syndromes of osteoporosis, type I and type II [Riggs et al., N Engl J Med 314:1676–1686 (1986); Riggs et al., J Clin Endocrinol Metab 70:1229–1232 (1990)]. The former, type I, or "postmenopausal", osteoporosis, occurs in a relatively small subset of women 48–65 years of age and is linked to events related to menopause. The latter, type II, or "senile", osteoporosis, occurs in women greater than 75 years of age, and is the final result of gradual, age-related decline in bone mineral density. In this context, it is evident that women who experience osteoporotic bone fractures in the type I setting have lost considerable bone density compared to most other women of the same age. Thus, it is not surprising that some authors have written of "fast-losers" and "slow-losers" of bone density, distinguished from each other most particularly in the perimenopausal period of life. It is in this heterogeneity of osteoporosis that the potential role of estrogen and estrogen metabolism is greatest. All women undergo a dramatic decline in circulating estrogen levels with menopause, yet only 10–20% of this population ("fast-losers") will experience relatively rapid diminution of bone mineral density. Certain nutritional and lifestyle factors, such as inadequate intake of calcium, may contribute to low bone mass independent of estrogen level, and this can further increase a woman's risk of developing postmenopausal osteoporosis.

Postmenopausal osteoporosis affects the entire skeleton. In the early postmenopausal years, bone loss averages 2% per year but can vary from <1% to >5%. In the early phase of postmenopausal bone loss, the rate of trabecular (cancellous) bone loss exceeds that of cortical bone, and by the end of the first postmenopausal decade, most white women have osteopenia or osteoporosis. Postmenopausal osteoporosis is more prevalent in white and Asian women than in women of other races. It is estimated that osteoporosis affects about 45 percent of all postmenopausal white women.

Low bone mass is a major feature of postmenopausal osteoporosis and the primary determinant of fracture. The relationship between bone mass and fracture risk is more powerful than that between serum cholesterol concentration and coronary artery disease. Fortunately, bone mass can be readily measured, preserved, and even increased, with therapeutic intervention.

Fracture is the most clinically significant complication of postmenopausal osteoporosis. Hip fractures are costly and clinically serious. Among patients with hip fracture, 12 to 20% die within 1 year after the fracture, and more than 50% of the survivors are unable to return to independent living. Spinal injuries, in particular, may also lead to other adverse effects: loss of height, Kyphosis (Dowager's hump), and back pain (acute and chronic). Osteoporotic fractures often occur at a site of low bone mass and are usually induced by trauma.

Assessment of risk factors can help the physician to identify women who are susceptible to fracture, formulate a clinical suspicion of osteoporosis, and develop an osteoporosis prevention program. Several factors associ be altered by the patient. A knowledge of all existing risk factors, when considered in conjunction with the bone mineral density (BMD) measurement, may also provide direction for intervention with a specific therapeutic agent. A woman may be arbitrarily considered to be osteopenic or osteoporotic if she has a BMD greater than 1, or greater than 1.5 standard deviations below that of the typical woman of her age, respectively.

It is now possible, using advanced techniques, to determine appendicular and axial skeletal bone mass conveniently with a measurement accuracy exceeding 95 percent. Of the available methods of measuring bone mineral density (BMD), single-photon and single X-ray absorptiometry (SPA and SXA) are applicable to the peripheral appendicular bones, and dual-energy X-ray absorptiometry (DEXA) is the optimal method used to estimate axial, proximal appendicular, and total bone mass. Bone-mass measurement has an increasingly important role in clinical decision-making. Although factors such as body size, cigarette smoking, and reproductive history are valuable in determining which women are most likely to develop osteoporosis, it is useful to have reliable, quantitative evidence that a woman is at increased risk for fracture, especially when therapy is instituted. BMD measurement at any axial (that is, hip, vertebra) or peripheral (that is, radius, calcaneus) site is useful for a one-time assessment of fracture risk. Currently, however, AACE (American Association of Clinical Endocrinology) recommends performing the first measurement at the hip. The hip is also a good site for the baseline and follow-up measurements when therapeutic intervention is planned. Ideally, if resources allow, measurements should be taken at both sites for baseline and follow-up because the trabecular bone of the spine produces the quickest therapeutic response. These BMD measurements are often expressed as Z-scores, which represent the standard deviation of a woman's BMD from the norm; osteopenics have BMD Z-Scores <−1, osteoporotics BMD Z Scores <−1.5 (American Association of Clinical Endocrinology Guidelines). These cutoffs are somewhat arbitrary, given the high variability of BMD between women at any age.

A number of prospective studies using bone-mass measurements to predict fractures have been undertaken. Although each of the studies contains unique features, each has shown that decreased bone density at the sites measured is associated with increased risk of fracture at the sites reported.

Such studies demonstrate that bone-mass measurement, compared with the standard for age and weight, can predict which women can experience a fragility fracture. These groups concluded that bone mineral measurements taken at a variety of skeletal sites have a moderate ability to predict for at least eight to ten years a fracture that might be related to osteoporosis. Calculations vary with each study because of differences in populations, measurement techniques, etc.

From the studies shown, it appears that measurement of BMD has the greatest predictive value in determining future hip fracture, with relative risk ranging from 1.3 to 2.7. As an example, for every 1 SD decrease in BMD at any site, a 2.6-fold increase occurs in the risk of hip fracture. When adjusted for age, this means that a woman whose BMD is 1 SD below the mean is about seven times more likely to have a hip fracture than a woman whose bone density is 1 SD above the mean. In addition, there appears to be a trend in the three studies that measured BMD at the hip. Measurement of BMD at the hip is associated with the highest range of relative risks for subsequent hip fracture.

In summary, the lifetime risk of death from complications of hip fracture is about 2.8 percent for 50-year-old white postmenopausal women. Bone mineral density (BMD) is a good predictor of hip, spine, and all-site fractures. BMD measured at the proximal femur predicts subsequent risk of hip fracture better than BMD measured at other skeletal sites. A number of epidemiologic studies have eof BMD and the prevalence of fractures. The studies have determined that, regardless of the type of measurement used or the site measured, decreased BMD leads to increased risk of fracture.

The mechanism for loss of mineral density (BMD) in mammalian bone has been and continues to be the subject of intense research. One of the most active areas is elucidation of the role of estrogens in the formation and resorption of minerals in estrogen-sensitive tissue compartments of the bone. The clear cut role of estrogens in inducing and conservation of BMD, and preventing hip fracture after menopause [Quigley et al. Am J Obstet Gynecol 156:1516–1523 (1987); Keil D et al. N Engl J Med 317:1169–1174 (1987)] has led to a long search for evidence of relative estrogen deficiency in women with osteoporosis. For example, Peak BMD is relatively low in women with primary amenorrhea or delayed puberty [Dhuper et al., J Clin Endocrinol Metab 71: 1083–1088 (1990)], and estrogen deficiency after menopause enhances the rate of bone turnover and results in an acceleration of bone loss [Civitelli et al., J Clin Invest 82:1268–1274 (1988)].

Studies of serum and urinary levels of estrogens in osteopenia and osteoporosis have, however, given negative, and often contradictory, results. Women lose bone at different rates up to 10 years after menopause, even though there is no significant differences in their total serum estradiol (E2) levels [Riis Am J Med 98: (Suppl 2A)29S–32S (1995)], or urinary estrone (E1) levels [Lim et al., J Clin Endocrin Metab 82: 1001–1006 (1997)] as determined by immunoassay or gas chromatography-mass spectroscopy (GC-MS), respectively. Bone mineral density in premenopausal women, however, does seem to depend upon their total, lifetime exposure to circulating estrogen levels [Civitelli et al. J Clin Invest 82:1268–1274 (1988)]. Moreover, the rate of bone loss in premenopausal women after complete oophorectomy is more rapid than in women undergoing natural menopause [Stepan et al., Bone 8:279–284 (1987), and Civitelli et al., J Clin Invest 82:1268–1274 (1988)]. The levels of plasma E1 and E2 may not accurately reflect the biologically available amount of estrogen in postmenopausal women because these primary estrogens are further oxidized by intercellular microsomal enzymes in bone and other tissues to metabolites that have either more or less potent estrogenic effects in bone. For example, the inventor and others have recently shown by immunochemical methods that the metabolism of estrogen is altered in peri- and post-menopausal American women with osteopenia or osteoporosis such that production of urinary metabolites of estrogen, namely 2-hydroxyestrone (2OHE1) and/or 16α-hydroxyestrone (16αOHE1) are increased in osteopenia [Hodge et al. J Bone Miner Res 10 (Suppl 1):S444 (1995)]. The later immunochemical studies of Hodge et al. found statistically significant negative correlations between BMD and urinary estrogen metabolites at several bone sites including spine and femur, but most especially between BMD and the lateral projections of the spine (VBD-LAT-tot). This initial finding, however, is in contrast to a recent study of urinary metabolites in Korean postmenopausal women by gas chromatography-mass spectrometry (GC-MS). Lim and colleagues [J Clin Endocrinol Metab 82:1001–1006 (1997)] reported a positive significant correlation between 16αOHE1 and spinal BMD, and a possible negative correlation between 2-hydroxyestradiol (2OHE2) and femoral BMD. No correlations were found by Kim et al. for other urinary estrogen metabolites or between metabolite levels and BMD at other bone sites. The association between 2OHE2 and femoral bone density observed by Kim et al. was not significant, as correlation was lost after correcting for age. The later investigators did not specify which spinal projection(s) was used to calculate spinal BMD, nor did they examine the correlations between estrogen metabolites and BMD at other important sites such as the hip, or specific projections of hip BMD. The similarities and differences between these later two studies, however, should be interpreted cautiously in light of the established differences in drug metabolism and lifestyle between caucasians and orientals [Lou, Drug Metab Rev 225:451–475 (1990)].

Most significantly, the studies of Kim et al. (1997) or Hodge et al. (1995) were not designed to correlate serum or urinary estrogen metabolites with the rate of bone loss, or change in BMD with time in postmenopausal women. Although there is a correlation between BMD and risk for fracture, many women with low BMD at menopause lose BMD very slowly thereafter, and never experience fractures, even after trauma. Conversely, many women with high BMD at menopause will experience rapid bone loss and subsequent bone fracture.

Independent of BMD, the most important single diagnostic parameter for effective detection and management of osteopenic pathologies is the rate of bone loss. Current methods use x-ray densitometry or dual x-ray absorptiometry (DEXA) to assess BMD. Although the accuracy of DEXA methods are said to be as high as ±3 percent of the BMD, aortic calcification, vertebral compression, degenerative arthritis, or other spinal conditions and diseases, amongst other factors, add a higher error to measurement of BMD [Nilas et al., Bone Miner 4:95–103 (1988)]. Moreover, changes in bone density over time are typically less than 5 percent/year in most postmenopausal osteopenics. Therefore, measurement intervals by DEXA for BMD of at least two years are needed before diagnostic confirmation of bone loss. Intermediate biomarkers of rate of bone loss, as in perimenopausal women, are needed to identify those women who can benefit from earlier treatment with estrogens, bisphosphonates, or other bone-conserving drugs. Although previous studies of serum and urinary estradiol and/or estrone in osteopenic women have yielded negative and contradictory results (see above), the dependence of BMD on estrogen suggests that some estrogen or its metabolite must be a marker for this physiological process. All women undergo a dramatic decline in circulating estrogen levels with menopause, yet only 10–20% of this population ("fast-losers") will experience relatively rapid diminution of bone mineral density. Preventive strategies depend upon identifying the clinical or biological characteristics of this small population, in order to target them for appropriate therapy. The levels of specific metabolites of estrone in physiological fluids from peri- and postmenopausal women will conceivably serve as such intermediate biomarkers.

The metabolism of estradiol, the ovarian estrogen, is primarily oxidative (FIG. 1). There is an initial oxidation of estradiol to estrone I, FIG. 1) which, in turn, is oxidized mainly by one of two alternative, irreversible pathways: 2-hydroxylation which leads to the relatively nonestrogenic metabolite 2-hydroxyestrone, and through activity of O-catechol methyl transferase (COMT), the inactive metabolite, 2-methoxyestrone (FIG. 1, VIII and VII, respectively); and 16α-hydroxylation which leads to the estrogenic metabolite 16α-hydroxyestrone (III, FIG. 1), among others. The relative contribution of the 16α-hydroxylation pathway is relatively constant under most biologic circumstances. There are at least two other oxidative pathways for estrogen; 4-hydroxylation which leads to 4-hydroxyestrone (4OHE1)(IX), and 15α-hydroxylation which leads to 15α-hydroxyestrone (15OHE1) (X). Alterations may also exist in conjugation of estrogens in tissues and body fluids. Research done on urinary estrogen metabolites indicates that urinary estrogens may be covalently conjugated as ethers or esters with glucuronic acids, and/or sulphates, respectively, at the steroidal hydroxyl groups. Much less is known about the nature of estrogen metabolites in tissues and other bodily fluids. Hypothetical conjugates of 16OHE1 as they might occur in tissues and/or body fluids are illustrated in FIG. 2, conjugates of 2OHE1 in FIG. 3, and conjugates of 2MeoE1 in FIG. 4.

In 1966, Zumoff and associates reported that men with breast cancer demonstrated markedly increased 16α-hydroxylation of estradiol [Zumoff et al. J Clin Endocrinol Metab 26: 960 (1966)]. These same investigators subsequently reported increased formation and excretion of urinary 16α-hydroxylated estrogen metabolites in women with breast cancer after injection of radiolabelled estradiol [Hellman et al. J Clin Endocrinol Metab 33:138–144 (1971)]. Using this radiometric method, Fishman and coworkers greatly extended the study of 16α-hydroxylation and 2-hydroxylation in breast cancer by reporting the following findings: 1) increased 16α-hydroxylation, but unchanged 2-hydroxylation of estrogen was confirmed in women with breast cancer [Schneider et al.: Proc Natl Acad Sci USA 79:3047–3051 (1982)]; 2) increased 16α-hydroxylation was found in women at familial high risk for breast cancer [Bradlow et al.: Ann NY Acad Sci 464:138–151 (1986)]; and 3) Increased 16α-hydroxylation was found in mouse strains with high incidence of breast cancer, and the degree of increased risk paralleled the increase in 16α-hydroxylation [Bradlow et al.: Proc Natl Acad Sci USA 82:6295–6299 (1985). By contrast, the aforecited radiometric studies found no significant alteration in 2-hydroxylation in breast cancer. No studies concerning bone metabolism or osteoporosis have been done using the radiometric method.

The radiometric method is, however, not applicable to routine medical practice, and is complicated by the necessity to normalize the amount of tritium released to the injected animal's body volume. Moreover, no information as to the amounts or kinds of estrogens transformed by 16α-hydroxylation of estradiol is obtained by a radiometric method. Recognizing the limitation of the radiometric method, Fishman and co-investigators attempted to develop a radioimmunoassay (RIA) for unconjugated 16OHE1 using polyclonal antisera to 16OHE1 and tritiated 16OHE1 as tracer [Ikegawa et al., J Steroid Biochem 18:329–332 (1983)]. RIAs done upon ethyl ether extracts of serum found very low levels of 16OHE1 in serum from normal men and women, averaging only 4–10 pg/mL in men and 5–16 pg/mL in women. Unfortunately, the researchers found that blank values for water, buffer, and steroid-free serum were also in the range of 5–18 pg/mL. The very low levels of 16OHE1 found in this assay, and its lack of reproducibility, obviously precluded its use in further studies of the role of 16α-hydroxylation in breast cancer, and there are no reports of its use in any further studies. Yoshizawa and Fishman, J Clin Endocr 32:3–6 (1971), also attempted to develop an RIA for unconjugated 2OHE1 in methylene chloride extracts of serum. The later RIA found significant differences between clinical groups studied, but this assay was never used in studies of animals with cancer or other proliferative diseases. Emons and coworkers, in Acta Endocr, Copenh. 91: 158–166 (1979), developed an indirect radioimmunoassay for 2-methoxyestrone in human plasma, but did not apply that assay to studies of estrogen metabolism in disease. These same immunoassays were subsequently used by these investigators, however, in studies of estrogen metabolites in urine.

These assays also used the radioimmunoassay method and determined total urinary 2OHE1 and 16OHE1 (normalized to urine creatinine concentration) after deconjugation of glucuronides and sulfates with enzyme treatment. For example, Michnovicz et al. in Steroids 52:69–83, 1988, found no significant difference in total urinary 16OHE1 secretion when comparing smokers and nonsmokers, but increased 2-hydroxylation in smokers; Galbraith and Michnovicz in N. Engl. J. Med 321:269–274, 1989, found no effect of cimetidine on urinary total 16OHE1 secretion, but reported a decrease in 2-hydroxylation; and, Michnovicz and Galbraith in Steroids 55:22–26, 1990, found no effect of thyroxine treatment on total 16OHE1 secreted in urine, but increased 2-hydroxylation with thyroxine treatment.

Finding no differences in urinary secretion of an individual urinary metabolite reflective of suspected alterations in estrogen metabolism associated with a specific pathologic condition, Fishman and coworkers developed a method for detecting alterations in estrogen metabolism which comprised isolating at least two metabolites of estrone from a biological sample and determining their quotient. This quotient, and/or changes in this quotient, are reported to be reflective of alterations in estrogen metabolism. This method forms the basis of European Patent Application No. 040917682 published Jan. 23, 1991. In regard to the utility of measurements of 16OHE1, the inventors state in this Application (page 2, line 24–25) that, ". . . the constitutive nature of this metabolite has discouraged its further consideration for either diagnostic or therapeutic purposes". Moreover, the method of Michnovicz et al. does not recognize the importance of measuring the said glucuronide fraction of the estrogen metabolites, that is, the conjugated forms of metabolites, and specifically, the 3-glucuronides.

As indicated above, several methods have been used to detect altered estrogen metabolism, especially increased 16α-hydroxylation in animals bearing tumors. These methods, however, have not been applied to research in osteoporosis, and are not applicable to human research and routine medical practice. Previous attempts to quantify 16OHE1 directly by RIA have failed to find measurable levels in serum. Therefore, there exists a need in the medical art for rapid, accurate, diagnostic tests for metabolites of estrone such as 2OHE1, 2MeoE1, and 16OHE1, assays that reflect altered metabolism and conjugation of estrogens in tissues and bodily fluids from animals. The invention disclosed herein meets said need by providing for non-invasive diagnostic/prognostic assays to detect and/or quantify in mammalian tissues and body fluids, preferably urine and plasma or serum, estrogen metabolites 2OHE1, 2MeoE1, and 16OHE1 and their conjugates, preferably as the sum of the free metabolite and its 3-glucuronide conjugate.

SUMMARY OF THE INVENTION

The present invention involves a method of screening for osteopenia in humans wherein an alteration in estrogen metabolism is indicative of low BMD, rapid loss of BMD leading to development of osteoporosis, or a susceptibility thereto. This method comprises detecting the level of a particular estrone metabolite from a biological sample taken from the mammal under examination, and comparing this level with an extrinsic numerical value derived either previously from the mammal under testing, or from the testing of other subjects of the same species, to detect increases or decreases in the level of the particular estrone metabolite and its 3-glucuronide (also called the 3-glucosiduronate) above or below that of healthy individuals . A highly preferred embodiment involves the testing of serum to measure the level of the inactive estrogens 2OHE1-3-glucuronide, 2MeoE1-3-glucuronide, and the active estrogen 16OHE1-3-glucuronide to detect and/or monitor the bone mineral density (BMD) and rate of loss of BMD in women. The predictive link between levels of these metabolites, as measured by the methods herein taught, and bone mineral metabolism, or bone mineral density, arises from the disclosed observations that exposure of estrogen-dependent tissues such as bone to higher levels of inactive estrogen metabolites such as 2OHE1 or 2MeoE1 results in relatively decreased bone mineral densities. Conversely, exposure of the mammal to higher levels of active estrogen metabolites such as 16OHE1 results in relatively increased bone mineral densities. The cumulative or net exposure of bone to estrogen may also be represented by some numeric combination of the active and inactive estrogen metabolites, as, for example, the the sum of 2MeoE1 plus 16OHE1, etc.

The very different conclusions drawn from the prior art and that of the instant invention are due to the following distinctions between the prior art and the instant invention:

1) The levels of estrogen metabolites 2OHE1, 2MeoE1, and 16OHE1, have not been previously measured by direct assay in urine or serum of osteopenic women; 2) 2OHE1, 2MeoE1, and 16OHE1 metabolites are not necessarily totally deconjugated prior to assay in the present invention; 3) a specific conjugate of each metabolite, substantially, the 2OHE1-, 2MeoE1-, and 16OHE1-3-glucuronides, are measured according to this invention, not the "free" 2OHE1, 2MeoE1, or 16OHE1; 4) the level of the 2OHE1-, 2MeoE1-, or 16OHE1-3-glucuronide in body fluids is useful by itself, without comparison or indexing to another estrogen metabolites or other substances; 5) The levels of 2OHE1-, 2MeoE1-, or 16OHE1-3-glucuronide in body fluids, and numerical combination thereof, are predictive for BMD, and the rate of loss of BMD in women.

OBJECTS OF THE INVENTION

It is thus an object of the present invention to provide diagnostic/prognostic methods useful for screening for osteopenic pathologies wherein an alteration in estrogen metabolism is indicative of said pathology or a susceptibility thereto.

It is a further object of the present invention to provide a method for such screening which measures the level of the 16OHE1-glucuronide fraction, i.e., the sum of 16α-hydroxyestrone (16OHE1) and its conjugate, 16OHE1-3-glucuronide.

It is a further object of the present invention to provide a method for such screening which measures the level of the 2OHE1-glucuronide fraction, i.e., the sum of 2-hydroxyestrone (2OHE1) and its conjugate, 2OHE1-3-glucuronide.

It is a further object of the present invention to provide a method for such screening which measures the level of total 2-hydroxylated metabolites of estrone, i.e., the sum of 2-hydroxestrone (2OHE1) and its conjugate, 2OHE1-3-glucuronide, 2-hydroxestrone (2OHE2) and its conjugate, 2OHE2-3-glucuronide, and 2-hydroxyestriol (2OHE3), and its conjugate, 2OHE3-3-glucuronide.

It is a further object of the present invention to provide a method for such screening which measures the level of the 2-MeoE1-glucuronide fraction, i.e., the sum of 2-methoxyestrone (2-MeoE1) and its conjugate, 2-MeoE1-3-glucuronide.

It is a further object of the present invention to provide a method for such screening which measures the level of total 2-methoxy metabilites of estrone, i.e., the sum of 2-methoxyestrone (2MEOF1) and its conjugate 2 MEOE-3-glucuronide, 2-methoxyestradiol (2MEOE2) and its conjugate 2MEOE2-3-glucuronide, and 2-methoxyestriol (2MEOE3), and its conjugate 2MEOE3-3-glucuronide.

It is a still further object of the present invention to measure the 16OHE1 glucuronide fraction, the 2OHE1-glucuronide fraction, or the 2-MeoE1-glucuronide fraction to detect and monitor bone mineral metabolism, especially in osteopenic states including osteoporosis.

It is yet another object of the present invention to provide for specific diagnostic/prognostic assays to detect and/or quantify the 16OHE1-glucuronide fraction, the 2OHE1-glucuronide fraction, or the 2-MeoE1-glucuronide fraction in tissues, tissue extracts, and bodily fluids of mammals, and thereby determine BMD, assess the rate of change in BMD, gain, stability, or loss, and provide valuable information for the diagnosis and prognosis of osteopenic disease.

A still further object of the present invention involves the preparation of test kits which contain the necessary reagents and protocol for the performance of assays which can be used for the aforementioned screening assays.

BRIEF DESCRIPTION OF THE DRAWING FIGURES

DESCRIPTION OF THE INVENTION

Figure 1:
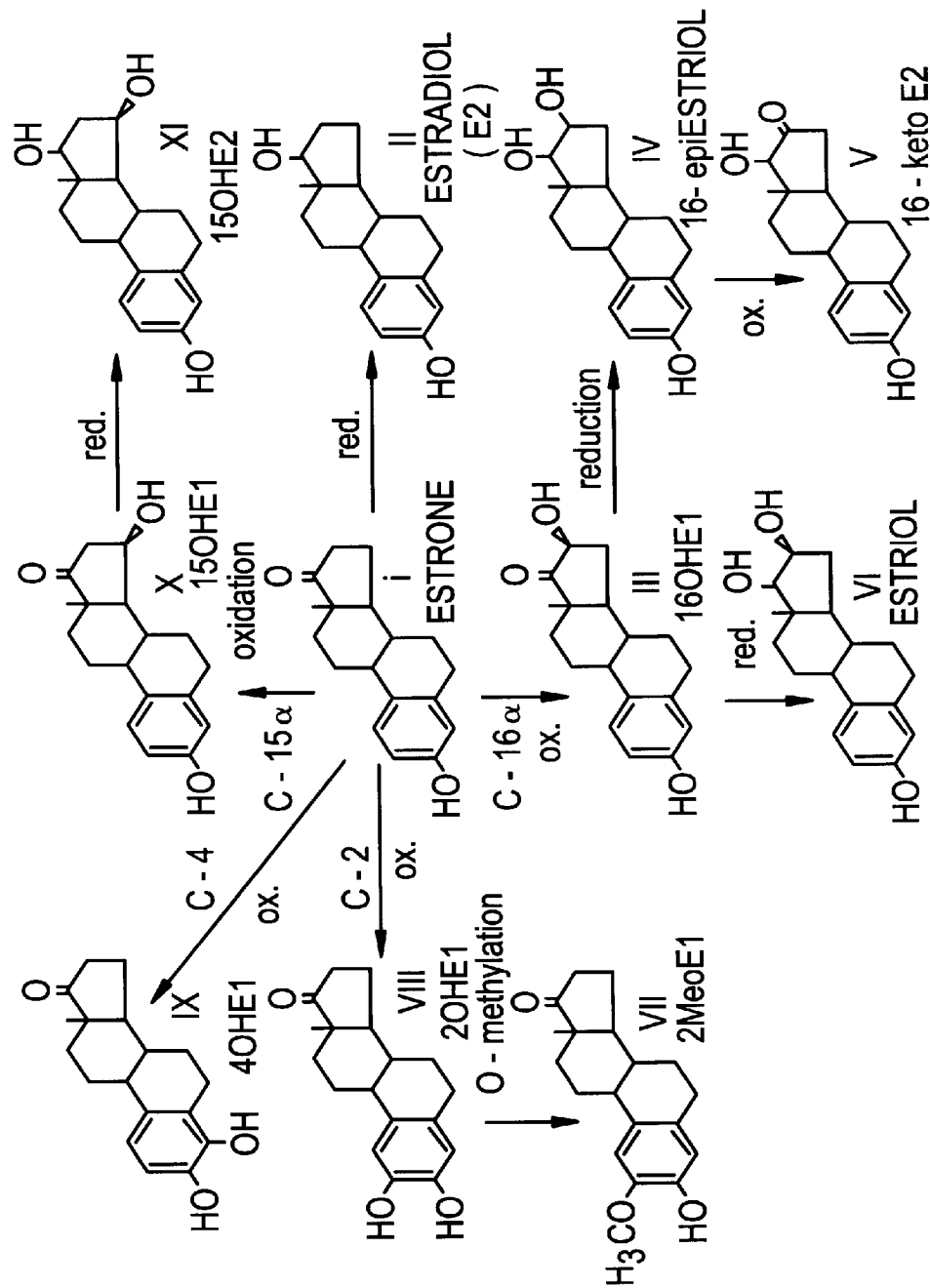
FIG. 1 is a chart illustrating the principal oxidative and reductive metabolites of estrone.

While not wishing to be bound by any particular theory, it is believed that previous methods to detect and/or quantify estrogen metabolites such as 16OHE1, as by immunological assays, have failed because investigators did not recognize that such metabolites, and especially 2OHE1, 2MeoE1, and 16OHE1 in tissues and bodily fluids exist predominantly in the form of glucuronides (also known as glucosiduronates) rather than as free, unconjugated species. Moreover, it was not known that it is the glucuronide fraction (free plus 3-glucuronide) that is altered most significantly in animals experiencing loss of bone mineral density (BMD). Further, investigators did not recognize that the physical-chemical nature of the estrone metabolite glucuronide, that is, its negative charge, its lipophilic nature, and ability to form Schiff's bases with amines, promote sequestration of glucuronide in tissues and bodily fluids, chiefly within protein. Therefore, immunological assays would not be able to detect and/or quantify the glucuronide fraction in tissues and body fluids unless the assays are done under specific conditions adapted to liberate the tightly bound glucuronide fraction, and high affinity, high specificity antibodies that recognize the glucuronide fraction are used.

The present invention overcomes the limitations of the prior art by utilizing in the practice of this invention antibodies which recognize epitopes on both the free estrone metabolite and its 3-glucuronide conjugate equivalently, thus providing assays that are able to simultaneously detect and/or quantify both the unconjugated and 3-glucuronide forms of the estrone metabolite. The novel buffer compositions, monoclonal antibodies, and assay methods taught herein enable nearly complete recovery of sequestered 2OHE1, 2MeoE1, 16OHE1 and their respective 3-glucuronides from tissues and bodily fluids with appropriate antibodies.

The Examples section illustrates the use of the 2OHE1-, 2MeoE1, and 16OHE1 glucuronide fractions in screening methods for use as intermediate biomarkers for detection and monitoring of osteopenic pathologies, including osteoporosis.

The diagnostic/prognostic methods illustrated herein can be used for the detection of osteopenic disease states. Also provided are compositions and test kits for implementing such methods. The discovery that said estrone metabolite glucuronide fraction is altered in human tissues and serum of women experiencing loss in bone mineral density has opened the way for the development of novel methods and compositions for the diagnosis and treatment of osteopenia and osteoporotic disease in humans and other mammals. The assays of this invention are both diagnostic and/or prognostic. The term "diagnostic/prognostic" is herein defined to encompass the following processes depending upon the clinical context: determining the presence, extent, and nature of the disease; predicting the most likely course and outcome of the disease; monitoring a patient for recurrence of disease; and, determining the preferred type and timing of therapy for a patient with osteopenia or osteoporosis.

In a highly preferred embodiment of the invention, the screening method disclosed herein utilizes the detection of 2MeoE1 and its conjugates at elevated levels in bodily fluids of mammals to determine which have reduced bone mineral density. The elevated portion of 2MeoE1 in urine and serum comprises substantially 2MeoE1-3-glucuronide and any free 2MeoE1, and is termed the "2MeoE1-glucuronide fraction". The detection and measurement of this fraction in urine provides highly useful methods for detecting the presence and extent of BMD in healthy mammals, and in mammals with osteopenic diseases, particularly in osteoporosis. The detection and measurement of this fraction in serum provides highly useful methods for detecting the rate of loss of BMD in osteopenic diseases, particularly in peri- and post-menopausal women with Type I osteoporosis.

Similarly, in a highly preferred embodiment, the screening method disclosed herein utilizes the detection of 2OHE1 glucuronide fraction at relatively high, moderate, or low levels in tissues and body fluids of mammals to predict the likelihood of bone mineral density loss, stability, or gain of an estrogen-sensitive osteopenic disease, particularly in osteoporosis.

Similarly, in a highly preferred embodiment, the screening method disclosed herein utilizes the detection of 16OHE1 glucuronide fraction at relatively high, moderate, or low levels in tissues and body fluids of mammals having osteopenia to predict the chance of bone mineral density loss, stability, or gain of an estrogen-sensitive osteopenic disease, particularly in osteoporosis.

Methods and compositions are provided for detecting and/or quantifying said 2OHE1-, 2MeoE1-, and 16OHE1-3-glucuronide fractions in tissues and bodily fluids. Further, diagnostic/prognostic methods are provided wherein other conjugated fractions of 2OHE1, 2MeoE1, and 16OHE1 are found in mammalian bodily fluids. For example, specific glycolytic and/or arylsulpholytic enzymes may be used to convert conjugates of 16OHE1 including 16OHE1-3, 16-glucuronide, 16OHE1-16-glucuronide, 16OHE1-3-sulphate, and 16OHE1-3-sulphate-16-glucuronide to unconjugated 16OHE1 or 16OHE1-3-glucuronide for assay in the described immunoassays of this invention.

Figure 2:
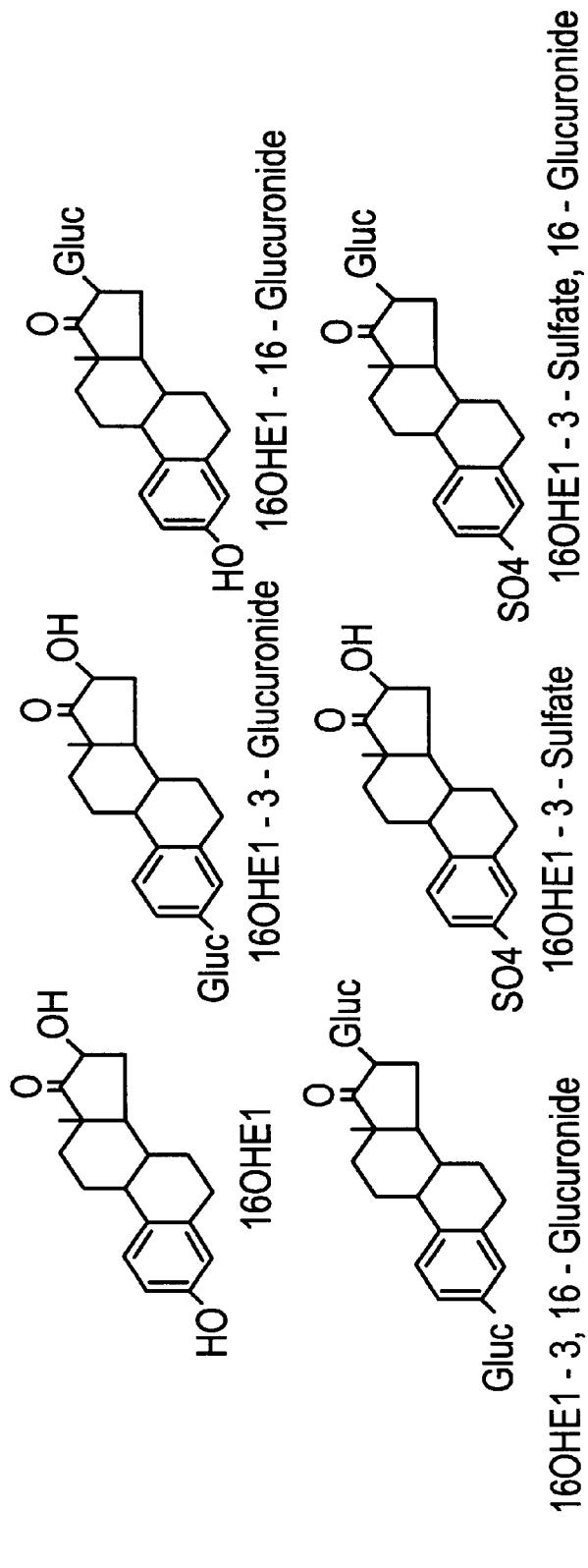
FIG. 2 is a chart showing the hypothetical conjugates of 16OHE1 as they might occur in tissues and/or body fluids of humans, and other mammals.

"Substantially" as used in the context of the "glucuronide fraction" indicates that although the estrone metabolite and its glucuronide conjugates are elevated in osteopenia, the significant, variable fraction of conjugated estrone metabolites in tissues and body fluids of mammals with osteopenic pathologies exists as the 3-glucuronide. It can be appreciated that an estrogen within the bodily fluids would be subject to a variety of metabolic processes, including glucuronidation and sulphation, among others. Further, it can be appreciated that cells within tissues under the influence of metabolic processes might conjugate estrogens differently than cells within normal healthy tissues. Moreover, a certain amount of the metabolite-3-glucuronide may be chemically or enzymatically converted to the "free" metabolite during isolation and/or immunological assay. Thus, by way of illustration, not limitation, the "16OHE1-glucuronide fraction" encompasses the sum of 16OHE1 and 16OHE1-3-glucuronides, as well as 16OHE1 conjugated at the 3-position with chemical moieties other than glucuronides (FIG. 2). Assays according to the present invention may detect and/or quantify 3-substituted 16OHE1, if the 3-substituent is a small sugar, an amino acid, or other small neutral or charged compound. The said 16OHE1-glucuronide fraction includes unconjugated 16OHE1 because a portion of 16OHE1-3-glucuronides may be converted to 16OHE1 by chemical (acid or base) or enzymic hydrolysis during isolation and/or processing of tissues or body fluids, as by endogenous glucuronidases or low or high pH.

Representative methods and compositions according to this invention include those for identifying patients who have a pathology associated with an alteration in estrogen metabolism, especially an osteopenic disease, and most especially, peri- and postmenopausal osteoporosis. An exemplary method comprises the steps of detecting the level of the said 2MeoE1-glucuronide fraction as described herein in a sample of patient's bodily fluid, and determining whether that level is elevated above normal. As shown herein, peri- and postmenopausal osteopenia is associated with increased metabolism of estradiol and estrone to its 2-methoxyestrone (2MeoE1) metabolites. Due to the metabolic processes by which they are derived, and their relatively antiestrogenic activities, an altered level of the 2OHE1- and/or 2MeoE1-glucuronide fraction in tissues and body fluids of a mammal, may be indicative of the presence of relatively reduced BMD, or be prognostic for progression of loss of BMD in estrogen-sensitive osteopenic pathology, especially peri- or postmenopasual osteoporosis.

In the practice of this invention, the animal tested is preferably human, and the bodily fluid tested is preferably serum or plasma, urine, or saliva. An important parameter of the status and likely outcome of the patient with osteopenia can be determined by testing a body fluid from the patient for elevated 2MeoE1-glucuronide fraction. Exemplary means of detecting and/or quantifying said 2MeoE1-glucuronide fraction, whether in mammalian body fluids, tissues or tissue extracts, include ligand binding assays, and immunoassays, among other means.

In the practice of this invention, bodily fluids may be collected from either men or women, and most preferably from perimenopausal or menopausal women. The invention may also be used in premenopausal women, taking into account normal menstrual variability in endogenous estrogen levels by collecting said bodily fluid at a specific point within the menstrual cycle, preferably at the immediate post-menses preovulatory stage, a method established in the prior art (Magini et al. J Steroid Biochem 36:523–526, 1990). The levels of estrogens in premenopausal women at this point within the menstrual cycle are sufficiently uniform for application of the present invention.

Immunoassays are the preferred means of detecting the 2OHE1-, 2MeoE1, or 16OHE1-glucuronide fractions, most preferably, a competitive inhibition immunoassay. In such an immunoassay format, antibodies specific to said 16OHE1-glucuronide fraction, 2MeoE1-glucuronide fraction, or 2OHE1-glucuronide fraction can be used with their paired respective 16OHE1-labeled, 2MeoE1-labeled, or 2OHE1-labeled enzymes, radioisotopes, fluorescent, or chemiluminescent tracers to compete with estrogen metabolite for binding to antibodies. Such antibodies can be prepared by methods known in the art, and described, for instance, in Klug et al., Steroids, Vol. 59, pp. 648–655 (1994).

An important parameter of the status and likely outcome of the patient with osteopenia can be determined by testing tissue, preferably fresh or formalin-fixed paraffin-embedded tissue sections. Exemplary means of detecting and/or quantifying said 2OHE1- or 16OHE1-glucuronide fraction in tissues include immunohistochemical detection, preferably with the alkaline phosphatase-anti-alkaline phosphatase (APAAP) method.

Further, assay results obtained according to the practice of this invention indicating the presence of abnormal levels of glucuronide fraction in body fluids or tissues of humans can be used in conjunction with results of other assays of bone disease, such as, for example, BMD as by DEXA analysis, markers of bone resorption, etc., to provide useful prognostic and diagnostic information.

Still further, the assays of this invention are useful for detection of osteopenic disease both pre- and post-diagnosis. For example, patients displaying elevated levels of said 2MeoE1-glucuronide fraction in early stages of osteopenia may be treated more aggressively, thus affording the patient a chance of increased conservation of BMD, with a reduction of the risk for fracture. By contrast, patients with low, or normal 2MeoE1-glucuronide fraction may be treated more conservatively, thus avoiding chemotherapeutic trauma, side-effects, and excess costs. Similarly, increases or decreases in the 2MeoE1-glucuronide fraction during therapy may correlate with, and corroborate, objective evidence of the patient's response to therapy. The levels of 2OHE1- and/or 16OHE1-glucuronide fraction can be similarly utilized.

The assays of this invention which indicate the presence of said glucuronide fraction in body fluids of humans are useful to detect and diagnose osteopenic pathologies, including screening of populations for low BMD or increased rate of bone loss, preferably when used adjunctively with other screening methods such as DEXA testing for BMD.

The invention also provides for test kits useful for the practice of the assays of the invention wherein said test kits comprise antibodies reactive with 2OHE1, 2MeoE1, 16OHE1 and/or said 2OHE1-, 2MeoE1-, and 16OHE1-glucuronide fractions, and enzymes, radioisotopes, fluorescers, or chemiluminescers as detection elements, in combination with containers, pipettes, slides, plate, coated well, etc., typically utilized as components of such test kits. The assays can be solid phase assays, but are not limited thereto, and can be in a liquid phase format, and can be based on enzyme-linked immunosorbent assays (ELISAs), radioimmunoassays, fluorometric assays, chemiluminescent assays, and particle agglutination assays, all of which may be amplified or unamplified through methods known in the diagnostic arts.

The concept underlying this invention is the discovery that patients suffering from a pathology associated with an alteration in estrogen metabolism have in their bodily fluids abnormal levels of metabolites of estrone, and the altered fraction of estrone metabolites associated with the pathology is, in a preferred embodiment, substantially the sum of the metabolite-3-glucuronide and unconjugated metabolite, herein designated the "glucuronide fraction". In the case of osteopenia and osteoporosis, relatively increased levels of said inactive estrogen glucuronide fractions will lead to lower BMD and increased rate of BMD loss; increased levels of active estrogen glucuronide fractions will lead to normal or increased BMD, and to decreased rate of BMD loss. The glucuronide fraction may thus be utilized as a novel intermediate marker of bone metabolism and BMD.

Assays for Estrogen Glucuronide Fractions in Mammalian Tissues and Body Fluids

Figure 3:
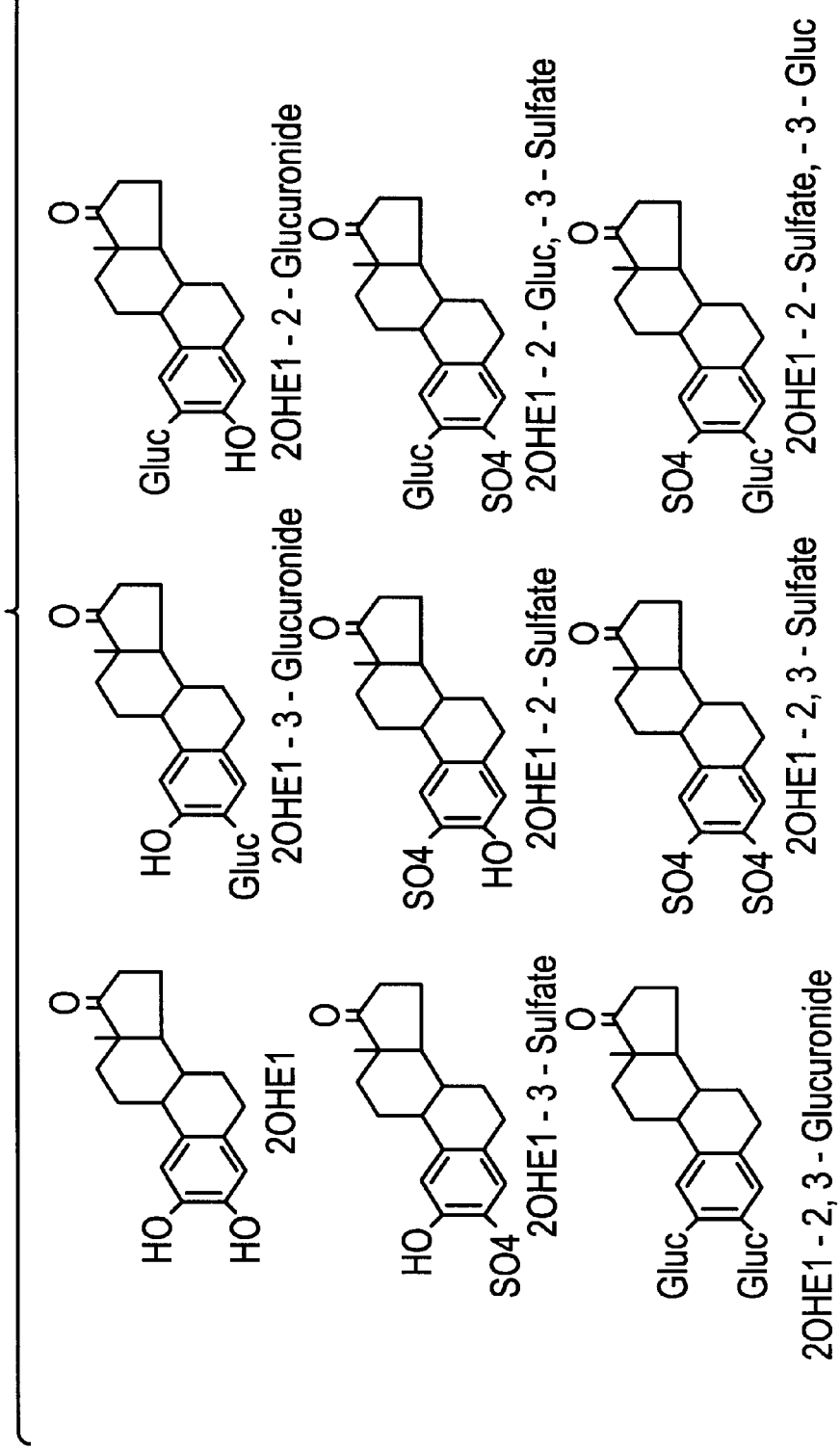
FIG. 3 is a chart showing the hypothetical conjugates of 2OHE1 as they might occur in tissues and/or body fluids of humans, and other mammals.
Figure 4:
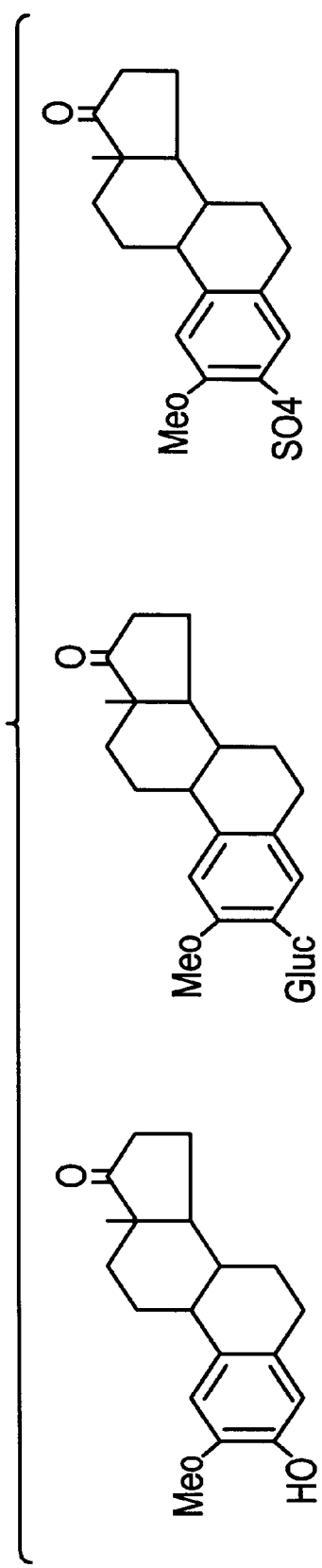
FIG. 4 is a chart showing the hypothetical conjugates of 2MeoE1 as they might occur in tissues and/or body fluids of humans, and other mammals.

Non-invasive diagnostic/prognostic assays are provided to detect and/or quantify said glucuronide fraction in body fluids of mammals, preferably humans. It can be appreciated that metabolites of estrone may be present in a patient's tissues and body fluids as, in the case of 16OHE1, unconjugated "free" metabolite, metabolite-3-glucuronide, metabolite-3,16-glucuronide, metabolite-16-glucuronide, metabolite-3-sulfate, or metabolite-3-sulfate, 16-glucuronide conjugates, among others (see FIG. 2). Said conjugates may be detected and/or quantified by the assays of this invention if they contain epitopes recognized by the antibodies of this invention. Certain conjugates of estrone metabolites may require pretreatment with enzymes prior to assay to remove conjugated groups that obscure the epitopes recognized by the antibodies of this invention. For example, treatment of 16OHE1-3,16-glucuronide with the enzyme β-glucuronidase, preferably enzyme derived from *E. Coli*, will reduce the former conjugate to 16OHE1 or 16OHE1-3-glucuronide, both recognized equally by antibodies of this invention. Treatment of 16OHE1-3-sulfate with the enzyme arylsulfatase, preferably that derived from the snail, *Helix Pomatia*, will reduce the former conjugate to 16OHE1, an estrogen recognized by antibodies of the present invention. Treatment of the mixed conjugate 16OHE1-3-sulfate, 16-glucuronide with a mixture of the enzymes β-glucuronidase and arylsulfatase described, will reduce the former 16OHE1 conjugate to 16OHE1. The exact use of these same enzymes with conjugates of 2OHE1 and 2MeoE1 (FIGS. 3 and 4) to obtain unconjugated and partially conjugated forms of 2OHE1 and 2MeoE1 is obvious to those skilled in the art.

The body fluids that are of particular interest in assaying for said glucuronide fraction according to methods of this invention include blood, serum, plasma, urine, breast exudate, saliva, sputum, cytosols, ascites, pleural effusions, and cerebrospinal fluid. Blood, serum, and plasma are preferred, and serum is the most preferred body fluid according to methods of this invention. The assays of this invention can also be used to detect and/or quantify the glucuronide fraction in tissues. Tissue preparations of particular interest include fresh tissue sections, fixed paraffin-embedded tissue sections, cell smears, cell suspensions, or freeze-mounted cells, preferably formalin-fixed paraffin-embedded tissue sections.

From a knowledge of the conjugates associated with osteopenic diseases, said glucuronide fraction as disclosed in this invention, monoclonal or polyclonal antibodies can be generated that specifically recognize the glucuronide fraction, that is, the 16OHE1 and 16OHE1-3-glucuronide, 2OHE1 and 2OHE1-3-glucuronide, and 2MeoE1 and 2MeoE1-3-glucuronide. Because the glucuronide fraction is found to be tightly bound to proteins, this fraction is not ordinarily found to exist freely in the tissues and body fluids of mammals. By the methods and materials utilized in this invention, however, the glucuronide fraction may be sufficiently liberated for binding by antibodies of this invention making detection and/or quantification possible. Utilizing current immunodiagnostic techniques that can quantify the binding of the glucuronide fraction to monoclonal antibodies of this invention, one can determine the amount of the glucuronide fraction in tissues and body fluids of osteopenic patients. Representative immunoassays involve the use of monoclonal antibodies and estrone metabolite-enzyme conjugates in competitive enzyme-linked immunoassays (ELISAs).

A preferred method to generate monoclonal antibodies involves covalently linking a metabolite, such as 2OHE1, 2MeoE1, or 16OHE1, to a protein and using it as an immunogen. Still further, the metabolite-glucuronide, such as 2OHE1-, 2MeoE1-, or 16OHE1-3-glucuronide, can be covalently linked to protein and be used as the antigen. By this method, many monoclonal antibodies recognizing and binding different conjugates of 16OHE1 or other estrone metabolites can be generated and selected, and such antibodies could be used to detect or identify differently conjugated fractions of 16OHE1 or other metabolites of estrone. Preferably, the monoclonal antibodies utilized in this invention are generated in mice after immunization with 2OHE1, 2MeoE1, or 16OHE1 covalently linked to keyhole limpet hemocyanin (KLH), and the individual antibodies are selected which recognize and bind both the unconjugated metabolite and its respective-3-glucuronide with high affinity and specificity.

The diagnostic/prognostic assays which utilize monoclonal antibodies according to this invention would typically involve obtaining a small amount of body fluid, preferably serum, from the mammalian, or human patient. The presence of the particular metabolite glucuronide fraction in serum can then be detected and/or quantified by a variety of immunodiagnostic techniques, including ELISA, RIA, and fluorescent, chemiluminescent assays, among others. For example, a representative of one type of ELISA test is a format wherein a microtiter plate is coated with, for example, monoclonal antibody to 16OHE1/16OHE1-3-glucuronide, and to the microtiter plate is added an appropriately treated sample of patient serum mixed with an enzyme covalently labeled with 16OHE1. After a period of incubation permitting competition between 16OHE1-enzyme and serum 16OHE1-glucuronide fraction for binding to monoclonal antibody bound to the solid phase, the plate is washed, and a color-generating enzyme substrate is added to determine the amount of 16OHE1-enzyme bound. The quantity of 16OHE1-glucuronide fraction in each serum sample is determined from the absorbance of the sample relative to a set of 16OHE1-glucuronide standards and controls of known concentration. The amount of inhibition of absorbance is directly proportional to the concentration of said 16OHE1-glucuronide fraction in each serum sample. It is apparent to one skilled in the art of diagnostic/prognostic assays that a wide variety of immunological assay methods are available for measuring the formation of antigen-antibody complexes. Numerous formats and protocols for immunodiagnostic assays are described in the scientific and patent literature. Exemplary immunoassays which are especially suitable for detecting a serum antigen include those described in U.S. Pat. Nos. 3,654,090, 3,850,752, RE 31,006 and 4,016,043. Antibodies employed in assays may be labeled or unlabeled. Suitable detection means include the use of labels such as enzymes, radioisotopes, fluorescers, chemiluminescers, particles, dyes, and the like. Such labeled reagents may be used in a variety of well known assay formats. See, for example, U.S. Pat. Nos. 3,654,090, 3,850, 752 and 4,016,043.

Competitive Direct Enzyme-linked Immunoassays for Estrogen Glucuronide Fractions A preferred assay format for the glucuronide fraction according to this invention is the competitive enzyme-linked immunoassay. Briefly, the concentration of the glucuronide fraction is determined by competitive binding between the glucuronide fraction in body fluids and metabolite-labeled enzyme for antibody to glucuronide fraction bound to a microtiter plate. Antibody bound to the solid phase provides a capture system for said glucuronide fraction, estrone metabolite-labeled enzyme. Higher concentrations of said glucuronide fraction in solution competitively inhibits binding of metabolite-labeled enzyme, and after equilibrium is reached, the amount of enzyme captured by antibody on the solid phase is determined by adding a colorless enzyme substrate which becomes colored after reacting with enzyme on the solid phase. The amount of glucuronide fraction is determined by reference to standards containing known amounts of the metabolite-3-glucuronide. A further competitive ELISA according to this invention reverses the orientation of antigen and antibody in the assay, wherein glucuronide fraction covalently coupled to protein is bound to the solid phase and antibody to said glucuronide fraction is labeled with enzymes.

There are many different embodiments of the competitive inhibition ELISA. For example, in a preferred format for 2OHE1, 2MeoE1, or 16OHE1 glucuronide fractions, rabbit antibody to mouse IgG, Fc-fragment specific (Jackson ImmunoResearch, Avondale, Pa., USA) is passively coated to the wells of a polystyrene microtiter plate (Maxisorb 8×12 plate, NUNC, Napierville, Ill., USA), wherein the coating volume is 150 $\mu$L, and the antibody concentration is 2 $\mu$g/mL in PBS. In such a preferred assay, bodily fluid diluted in an appropriate buffer is mixed in solution with a monoclonal antibody to said 16OHE1-glucuronide fraction, preferably the monoclonal antibody clone 19H7 (described below), and 16OHE1-labeled enzyme, preferably 16OHE1-alkaline phosphatase (AP, Sigma Chemical Co., St. Louis, Mo., USA). It is preferred that there be 5–10 ng/mL of monoclonal antibody, and 0.5–1 U/mL of 16OHE1-labeled AP in a reaction volume of 150 uL. It is preferred that body fluid, preferably serum be diluted 1:4 to 1:20 in the assays of this invention.

It is preferred that 16OHE1 derivatives for conjugation to enzymes and other proteins be synthesized as described by Ikegawa and Fishman, Steroids, 39:557–567, 1982, and be linked to enzyme, preferably AP, following Mattox, Litwiller, and Nelson in J. Steroid Biochem. 10:167–172, 1979. A preferred method for preparing estrone metabolite-3-glucuronide and estrone metabolite-3-glucuronide-labeled enzymes and proteins for use according to this invention is isolation from late pregnancy urine and conjugation to enzymes and proteins as described by Samarajeewa, et al., Steroids 36:611–618, 1980.

Preferred hydrogen ion buffers for assays of this invention are those commonly known as "Good" buffers as described by Good et al. in Biochemistry 5: 467–477, 1966, and in Analytical Biochemistry 104:300–310, 1980. These buffers are typically zwitterionic amino acids, either N-substituted taurines or N-substituted glycines, and are preferred because these compounds assist in disrupting the interactions between the said glucuronide fraction and proteins in tissues and body fluids. These buffer salts achieve this effect through ion-pair formation with the negatively charged glucuronides, and by their amphiphilic nature, promote the base catalyzed hydrolysis of Schiff's bases between the glucuronide fraction and primary amino groups on proteins. Further, it is preferred that the buffers of assays of this invention be kept acidic (pH<7.0) to protonate the glucuronide fraction, thereby minimizing charge interactions with proteins in tissues and body fluids. A good buffer with a pKa equal to the pH of the assay buffer system is preferred. Assays described in this typically invention utilize the Good buffer 2-(N-Morpholino)ethane sulfonic acid (MES).

The assays of this invention are preferably performed at temperatures between 0 and 15 degrees Centigrade.

Immunocytochemical Assays

A preferred assay method for the detection and/or quantification of said glucuronide fraction in tissues according to this invention is the inmmunoenzymatic labeling procedure utilizing the "unlabeled antibody bridge", preferably, the alkaline phosphatase: anti-alkaline phosphatase (APAAP) technique, and fixed tissue sections, preferably formalin-fixed paraffin-embedded tissue sections. In this method, prepared glass slide mounted tissue sections are incubated sequentially with: 1) mouse monoclonal antibody to the glucuronide fraction; 2) rabbit polyclonal anti-mouse IgG antiserum; and 3) mouse anti-alkaline phosphatase:alkaline phosphatase immune complexes (APAAP). The rabbit anti-mouse IgG acts to bridge the primary monoclonal antibody the APAAP complex, linking the two together. The presence of tissue-bound APAAP, and hence tissue-bound antibody to the said glucuronide fraction, is visualized by incubation of the treated tissue with a color producing substrate for alkaline phosphatase, preferably naphthol phosphate, as coupling reagent and Fast Red as capture agent, yielding a bright red color. There are many different embodiments of the immunoenzymatic "unlabeled antibody bridge" technique including those using the peroxidase:anti-peroxidase (PAP) technique.

In a preferred format for the glucuronide fraction, glass slide mounted formalin-fixed paraffin-embedded sections, preferably 4 to 10 $\mu$m thick, are deparaffinized with n-decane, rehydrated, and incubated with monoclonal antibody to said glucuronide fraction in TBS. The tissue is washed extensively with TBS, incubated for 1 hour with rabbit antibody to mouse IgG, is washed with TBS, and incubated with APAAP complex for 30 min. After a final wash with TBS, bound primary monoclonal antibody to the 16OHE1-glucuronide fraction is detected and/or quantified by incubating with a mixture of naphthol phosphate and Fast Red in diethanolamine buffer, pH 8.9, for about 10 minutes, or until intense red color is produced. Levamisole (5 mM) is included in the substrate buffer to inhibit endogenous alkaline phosphatase activity in tissues. Commercial APAAP kits containing reagents for use with murine monoclonal antibodies are available for the described procedure, preferably that manufactured by DAKO Corporation, Carpenteria, Calif., USA (Product No. 670K). The concentrations of all reagents are adjusted to optimize development of specific staining, while keeping non-specific background staining to a minimum. General techniques and principles of immunolabeling of monoclonal antibodies by the APAAP technique are discussed further by Mason in *Techniques in Immunocytochemistry*, Vol. 3, pp. 25–42, Bullock and Petrusz, eds., Academic Press, 1985.

Test Kits

The above assay according to this invention can be embodied in test kits to detect and/or quantify the estrogen metabolite-glucuronide fraction in mammalian, preferably human, tissues and body fluids wherein such test kits comprise antibodies, monoclonal and/or polyclonal, that can recognize epitopes on the estrogen metabolite-glucuronide fraction. Such diagnostic/ prognostic kits, for instance in the case of 16OHE1-glucuronide fraction, can further comprise, alone or in combination with the afore mentioned antibodies to said 16OHE1-glucuronide fraction, labeled 16OHE1 and/ or labeled 16OHE1-3-glucuronide, 16OHE1 and/or 16OHE1-3-glucuronide standards dispersed in tissues or body fluids, as well as positive and/or negative controls, and other reagents as necessary to perform the assays according to this invention. Similar kits for 2OHE1 and 2MeoE1 glucuronide fraction may be readily constructed using similar apparatus and the appropriate reagents.

Preparation of Monoclonal Antibodies

Monoclonal antibodies useful in this invention can be obtained by the well established process of cell fusion as described by Milstein and Kohler in Nature 256:495–497, 1975, and, more preferably, for antibodies to the 16OHE1-glucuronide fraction and 16OHE1-3-glucuronide for assays according to this invention, as described by Lane, et al., in Methods of Enzymology 121:183–192, 1986.

MAbs 12C2, 12D7, 16F11, and 19H7 to 16OHE1-glucuronide Fraction

All monoclonal antibodies were made by fusing splenocytes from female Balb/C mice immunized with 16OHE1-KLH estrogen: protein conjugates with non-immunoglobulin secreting murine myeloma cell line SP2/O-AG14 (ATCC CRL1581). Preferrably, the 16OHE1 derivatives for conjugation to enzymes and other proteins are synthesized as described by Ikegawa et al., in Steroids 39:557–567, 1982, and are linked to protein following the procedures Mattox, et al., in J. Steroid Biochem. 10:167–172, 1979. A preferred method for preparing 16OHE1-3-glucuronide and 16OHE1-3-glucuronide-labeled enzymes and proteins for use according to this invention is isolation from late pregnancy urine and conjugation to enzymes and proteins as described by Samarajeewa, et al., in Steroids 36:611–618, 1980.

In a representative protocol 10–14 week old female Balb/C mice were immunized i.p. with 50–100 µg of 16OHE1-KLH conjugate in 0.5 mL of TiterMax adjuvant (CytRx Corporation, Norcross Ga., USA) in PBS (50:50 v/v). Animals were boosted i.p. with 50–100 µg of emulsified antigen in TiterMax at monthly intervals for three months, or until mice demonstrated antibody to conjugate. Mice were bled and tested for antibody to 16OHE1/16OHE1-3-glucuronide every two weeks in an ELISA (described below). Mice with highest titers were injected intravenously with 100 µg of 16OHE1-KLH in sterile saline via the tail vein 4 days prior to cell fusion. Splenocytes from boosted mice were fused with SP2/O-AG14 mouse myeloma fusion partner cells using the high efficiency fusion protocol described by Lane, Crissman, and Ginn (see reference above). Spleen cells at 5:1 ratio with SP2/O cells were fused with 30% polyethylene glycol 1000, and distributed in 0.13 mL aliquots into twenty-five 96-well culture plates at $4 \times 10^4$ cell per well in media containing Hybridoma Enhancing Medium (HEM, Sigma Chemical Company, St. Louis, Mo. USA). A super-rich growth medium consisting of HY medium (90% DMEM, high glucose, 10% NCTC 135), 20% fetal bovine serum, 4 Mm L-glutamine, 20% HEM, and 30 µg/mL carboxyethyl gama-amino butyric acid (GABA) was used for feeding and subcloning. Selection for hybridoma cells was with hypoxanthine and azaserine. Each well was tested for antibody to 16OHE1/16OHE1-3-glucuronide when it became confluent with hybrid cells. All of the wells were tested over a three week period, and positive hydrids were cloned twice by limiting dilution in super rich medium without azaserine.

The presence of antibodies to 16OHE1-glucuronide fraction and/or 16OHE1-3-glucuronide was determined by a specific ELISA. Microtiter plates were coated 16 hours with rabbit anti-mouse IgG in PBS. The plates were blocked with 1% BSA in PBS for 1 hour, and after washing, culture supernatants (100 µL/well) were added to the plates and incubated for 2 hours. Plates were washed, and 16OHE1-alkaline phosphatase (300 U/mL) diluted 1:2000 with 0.1% gelatin in PBS was added. After a 1 hour incubation, plates were washed with PBS containing 0.05% Tween-20, and enzyme substrate, 3.8 µM paranitrophenylphosphate in 1M diethanolamine with 1 mM $MgCl_2$, pH 9.8 was added. The presence of antibody to 16OHE1-glucuronide fraction was seen by the development of a yellow color read at 405 nm in a microtiter plate reader. The isotypes of monoclonal antibodies were determined similarly, except that rabbit anti-mouse IgG heavy chain- and/or light chain-specific antibody: alkaline phosphatase conjugates were used (Zymed, San Francisco, Calif. USA).

Mab 4C11 to 2OHE1-Glucuronide Fraction

All monoclonal antibodies were made by fusing splenocytes from female Balb/C mice irnmunized with 2-Hydroxyestrone (2OHE1)-KLH estrogen: protein conjugates with non-immunoglobulin secreting murine myeloma cell line SP2/O-AG14 (ATCC CRL1581). Preferably, the 2OHE1 derivatives for conjugation to enzymes and other proteins are synthesized as described by Ball et al. in Steroids 31:249–258, 1978 and are linked to protein following Mattox, et al., in J Steroid Biochem 10:167–172, 1979. Following these methods, the 2OHE1 derivatives are prepared as the 17-carboxymethyloxime and linked to proteins through the C-17 position of 2OHE1. A preferred method for preparing 2OHE1-3-glucuronide and 2OHE1-3-glucuronide-labeled enzymes and proteins for use according to this invention is isolation from late pregnancy urine and conjugation to enzymes and proteins as described by Samarajeewa, et al., in Steroids 36:611–618, 1980.

In a representative protocol, 10–14 week old female Balb/C mice were immunized i.p. with 50–100 µg of 2OHE1-KLH conjugate in 0.5 mL of TiterMax adjuvant (CytRx Corporation, Norcross Ga., USA) in PBS (50:50 v/v). Animals were boosted i.p. with 50–100 µg of emulsified antigen in TiterMax at monthly intervals for three months, or until mice demonstrated antibody to conjugate. Mice were bled and tested for antibody to 2OHE1 every two weeks in an ELISA similar to that used for antibodies to 2MeoE1 (described below). Mice with highest titers were injected intravenously with 100 µg of 2OHE1-KLH in sterile saline via the tail vein 4 days prior to cell fusion. Spleen cells at 5:1 ratio with SP2/O cells were fused with 30% polyethylene glycol 1000, and distributed in 0.2 mL aliquots into ten 96-well culture plates at $2 \times 10^4$ cell per well in media containing Hybridoma Enhancing Medium (HEM, Sigma Chemical Company, St. Louis, Mo. USA). The growth media consisted of RPMI 1640, 10% heat-inactivated fetal bovine serum, 0.1 mM MEM nonessential amino acids, 2 mM glutamine, and HAT (hypothanxine/aminopterin/thymidine; 100:0.4: $16 \times 10^{-6}$ M). After a majority of the hybridomas had grown to confluence (about 10–14 days), all 960 wells were screened simultaneously for antibodies to 2OHE1.

The presence of antibodies to 2OHE1 and/or 2OHE1-glucuronide fraction was determined by a specific ELISA as described above for antibodies to 16OHE1 using 2OHE1-17-linked alkaline phosphatase. The isotypes of monoclonal antibodies were determined similarly, except that rabbit anti-mouse IgG heavy chain and/or light chain-specific antibody: alkaline phosphatase conjugates were used (Zymed, San Francisco, Calif. USA).

MAb 9D3 to 2MeoE1-Glucuronide Fraction

All monoclonal antibodies were made by fusing splenocytes from female Balb/C mice immunized with 2-Methoxyestrone (2MeoE1)-KLH estrogen: protein conjugates with non-immunoglobulin secreting murine myeloma cell line SP2/O-AG14 (ATCC CRL1581). Preferably, the 2MeoE1 derivatives for conjugation to enzymes and other proteins are synthesized as described by Ball et al. in Steroids 31:249–258, 1978 and are linked to protein following Mattox, et al., in J Steroid Biochem 10:167–172, 1979. Following these methods, the 2MeoE1 derivatives are prepared as the 17-carboxymethyloxime and linked to proteins through the C-17 position of 2MeoE1. A preferred method for preparing 2MeoE1-3-glucuronide and 2MeoE1-3-glucuronide-labeled enzymes and proteins for use according to this invention is isolation from late pregnancy urine and conjugation to enzymes and proteins as described by Samarajeewa, et al., in Steroids 36:611–618, 1980.

In a representative protocol, 10–14 week old female Balb/C mice were immunized i.p. with 50–100 μg of 2MeoE1-KLH conjugate in 0.5 mL of TiterMax adjuvant (CytRx Corporation, Norcross Ga., USA) in PBS (50:50 v/v). Animals were boosted i.p. with 50–100 μg of emulsified antigen in TiterMax at monthly intervals for three months, or until mice demonstrated antibody to conjugate. Mice were bled and tested for antibody to 2MeoE1 every two weeks in an ELISA similar to that used for antibodies to 16OHE$_1$ (described above). Mice with highest titers were injected intravenously with 100 μg of 2MeoE1-KLH in sterile saline via the tail vein 4 days prior to cell fusion. Spleen cells at 5:1 ratio with SP2/O cells were fused with 30% polyethylene glycol 1000, and distributed in 0.2 mL aliquots into ten 96-well culture plates at $2 \times 10^4$ cell per well in media containing Hybridoma Enhancing Medium (HEM, Sigma Chemical Company, St. Louis, Mo. USA). The growth media consisted of RPMI 1640, 10% heat-inactivated fetal bovine serum, 0.1 mM MEM nonessential amino acids, 2 mM glutamine, and HAT (hypothanxine/aminopterin/thymidine; 100:0.4: $16 \times 10^{-6}$ M). After a majority of the hybridomas had grown to confluence (about 10–14 days), all 960 wells were screened simultaneously for antibodies to 2MeoE1.

The presence of antibodies to 2MeoE1 and/or 2MeoE1-glucuronide fraction was determined by a specific ELISA as described above for antibodies to 16OHE1 using 2MeoE1-17-linked alkaline phosphatase. The isotypes of monoclonal antibodies were determined similarly, except that rabbit anti-mouse IgG heavy chain and/or light chain-specific antibody: alkaline phosphatase conjugates were used (Zymed, San Francisco, Calif. USA).

Characterization of Monoclonal Antibodies

All cell lines which bound 16OHE1-alkaline phosphatase underwent at least two subclonings by limiting dilution to insure monoclonality prior to characterization.

Specificities of antibodies to 16OHE1 metabolites were determine by a competitive inhibition ELISA, but with decreasing concentrations of (10 to 0 μg/mL) of the estrogen, androgen, or non-steroidal compound to be tested for cross-reactivity. The specificity of each monoclonal antibody for its antigen was defined as per cent cross-reactivity, and reflects the relative affinities of the antibody for different antigens. Cross-reactivity was defined as the ratio of concentrations of tested compounds to concentration of 16OHE1 required to give 50% inhibition of 16OHE1-labeled enzyme binding in the competitive ELISA, times 100. Monoclonal antibodies to 16OHE1 were tested for specificity against 16OHE1 conjugates and against structurally related estrogen and androgen metabolites, particularly against 16α-hydroxylated steroids. Monoclonal antibodies for use in the present invention were selected to react nearly equivalently with 16OHE1 and 3-substituted 16OHE1, that is to react with said 16OHE1-glucuronide fraction.

The relative affinities of monoclonal antibodies to 16OHE1 metabolites were determined by doing the competitive inhibition ELISA with decreasing amounts of 16OHE1 (1000 to 0 pg/mL) in the presence of a fixed amount of 16OHE1-alkaline phosphatase and monoclonal antibody in the wells of a microtiter plate (see Competitive Direct Enzyme-linked Immunoassay, above). Affinities were estimated assuming that the concentration of estrogen at 50% inhibition in the ELISA equals the reciprocal of the association constant, $K_a$.

The specificity and affinity of four monoclonal antibodies to 16OHE1 for use in the assays of the present invention are given in Table 1. All antibodies demonstrated similar apparent reactivities with 16OHE1 and 16OHE1-3-glucuronide (100±15%), and of the twelve metabolites tested, significant cross-reactivity of about 3% was seen for only 5-androsten-3β,16α-diol-17-one and 5α-androstan-3β,16β-diol-17-one. These 16α-ol-17-one androgens cross-react because their flat A/B-rings and equatorial 3-hydroxyl groups allows them to partially "fit" the anti-16OHE1 antibody binding site. These metabolites are only found at measurable concentrations during the last trimester of pregnancy. The affinities ($K_a$) of the monoclonal antibodies varied from 0.5 to $5 \times 10^{11}$ L/Mole. The isotype of all antibodies to said 16OHE1-glucuronide fraction is IgG$_1$ with lambda light chain.

All cell lines which bound 2OHE1-alkaline phosphatase underwent at least two subclonings by limiting dilution to insure monoclonality prior to characterization. Specificities of antibodies to 2OHE1 metabolites were determined by a competitive inhibition ELISA, but with decreasing concentrations of (10 to 0 μg/mL) of the estrogen, to be tested for cross-reactivity, as described above for monoclonal antibodies to 16OHE1. Monoclonal antibodies to 2OHE1 were tested for specificity against 2OHE1 conjugates and against structurally related estrogens, particularly against 2-methoxylated steroids. Monoclonal antibodies for use in the present invention were selected to react nearly equivalently with 2OHE1 and 3-substituted 2OHE1, that is to react with said 2OHE1-glucuronide fraction.

The relative affinities of monoclonal antibodies to 2OHE1 metabolites were determined by doing the competitive inhibition ELISA with decreasing amounts of 2OHE1 (1000 to 0 pg/mL) in the presence of a fixed amount of 2OHE1-alkaline phosphatase and monoclonal antibody in the wells of a microtiter plate (see Competitive Direct Enzyme-linked Immunoassay, above).

The specificity and affinity of one monoclonal antibody to 2OHE1-glucuronide fraction for use according to the present invention is given in Table 2. The antibody demonstrates similar apparent reactivities with 2OHE1 and 2OHE1-3-glucuronide (80%), and of the 10 metabolites tested, significant cross-reactivity was seen for all other 2-hydroxylated estrogens, 2-hydroxyestradiol and 2-hydroxyestriol. The affinity ($K_a$) of the monoclonal antibody is about $1 \times 10^{11}$ L/Mole. The isotype of all antibodies to said 2OHE1-glucuronide fraction is IgG$_1$ with kappa light chains.

The specificity and affinity of one monoclonal antibody to 2MeoE1-glucuronide fraction, 9D3, for use according to the present invention is given in Table 3. The antibody demonstrates similar apparent reactivities with 2MeoE1 and 2MeoE1-3-glucuronide (120%), and of the 10 metabolites tested, significant cross-reactivity was seen for all other 2-methoxylated 2-hydroxyestrogens; 2-methoxy 2-hydroxyestradiol and 2-methoxy 2-hydroxyestriol. The affinity ($K_a$) of the monoclonal antibody is about $2 \times 10^{11}$ L/Mole. The isotype of all antibodies to said 2MeoE1-glucuronide fraction is $IgG_{1, 2b}$ (mixed type) with lambda light chains.

TABLE 1

Specificity and Affinity of Monoclonal Antibodies to 16α-Hydroxyestrone

| Steroid Metabolite | % CROSS-REACTIVITY Monoclonal Antibody Designation | | | |
|---|---|---|---|---|
| | 12C2 | 16F11 | 19H7 | 12D7 |
| 1,3,5[10]-Estratrien-3,16α-diol-17-one (16OHE1) | 100.0 | 100.0 | 100.0 | 100.0 |
| 1,3,5[10]-Estratrien-3,16α-diol-17-one-3-glucuronide | 90.0 | 90.0 | 90.0 | 90.0 |
| 5-Androsten-3β,16α-diol-17-one | 3.6 | 3.0 | 3.6 | 3.3 |
| 5α-Androstan-3β,16α-diol-17-one | 3.0 | 3.2 | 3.1 | 3.1 |
| 4-Androsten-16α-ol-3,17-dione | 0.8 | 0.5 | 0.2 | 0.5 |
| 5α-Androstan-3α,16α-diol-17-one | 0.8 | 0.5 | 0.2 | 0.5 |
| 5β-Androstan-3α,16α-diol-17-one | 0.0 | 0.0 | 0.0 | 0.0 |
| 5β-Androstan-3β,16α-diol-17-one | 0.0 | 0.0 | 0.0 | 0.0 |
| 1,3,5[10]-Estratrien-3,16α,17α-triol | 0.7 | 0.6 | 0.5 | 0.9 |
| 1,3,5[10]-Estratrien-3,17β-diol-16-one | 0.2 | 0.2 | 0.2 | 0.2 |
| 1,3,5[10]-Estratrien-3.16α,17β-triol | <0.1 | <0.1 | <0.1 | <0.1 |
| 1,3,5[10]-Estratrien-3,17β-diol | <0.1 | <0.1 | <0.1 | <0.1 |
| 1,3,5[10]-Estratrien-3-ol-17-one | <0.1 | <0.1 | <0.1 | <0.1 |
| ISOTYPE (all IgG1, lambda light chain) | IgG1 | IgG1 | IgG1 | IgG1 |
| AFFINITY ($K_a$, L/mole × $10^{11}$) | 5.0 | 3.0 | 2.0 | 0.5 |

TABLE 2

Specificity and Affinity of Monoclonal Antibody to 2-Hydroxyestrone

| Steroid Metabolite | % CROSS-REACTIVITY Monoclonal Antibody Designation 4C11 |
|---|---|
| 1,3,5[10]-Estratrien-3-ol-17-one (2OHE1) | 100.0 |
| 1,3,5[10]-Estratrien-3-ol-17-one-3-glucuronide (2OHE1-3-glucuronide) | 80.0 |
| 1,3,5[10]-Estratrien-3,17β-diol-2 (2OHE2) | 100.0 |
| 1,3,5[10]-Estratrien-2,3,16,17β-tetrol (2OHE3) | 70.0 |
| 1,3,5[10]-Estratrien-3,4-diol-17-one | 2.1 |
| 1,3,5[10]-Estratrien-3,16α,17β-triol | 0.2 |
| 1,3,5[10]-Estratrien-3,17β-diol-16-one | 0.0 |
| 1,3,5[10]-Estratrien-3-ol-17-one | 0.2 |
| 1,3,5[10]-Estratrien-3,17β-diol | 0.0 |
| 1,3,5[10]-Estratrien-2,3-diol-17-one 2-methyl ether | 0.0 |
| ISOTYPE (IgG1, kappa light chain) | IgG1 |
| AFFINITY ($K_a$, L/mole × $10^{11}$) | 1.0 |

TABLE 3

Specificity and Affinity of Monoclonal Antibody to 2-Methoxyestrone

| Steroid Metabolite | % CROSS-REACTIVITY Monoclonal Antibody Designation 9D3 |
|---|---|
| 1,3,5[10]-Estratrien-3-ol-17-one-2-methoxy (2MeoE1) | 100.0 |
| 1,3,5[10]-Estratrien-3-ol-17-one-2-methoxy-3-glucuronide (2MeoE1-3-glucuronide) | 120.0 |
| 1,3,5[10]-Estratrien-3,17β-diol-2-methoxy (2MeoE2) | 100.0 |
| 1,3,5[10]-Estratrien-3,16,17β-triol-2-methoxy (2MeoE3) | 70.0 |

TABLE 3-continued

Specificity and Affinity of Monoclonal Antibody to 2-Methoxyestrone

| Steroid Metabolite | % CROSS-REACTIVITY Monoclonal Antibody Designation 9D3 |
|---|---|
| 1,3,5[10]-Estratrien-17-one-2,3-dimethoxy | <0.1 |
| 1,3,5[10]-Estratrien-3,16α,17α-triol | 0.0 |
| 1,3,5[10]-Estratrien-3,17β-diol-16-one | 0.0 |
| 1,3,5[10]-Estratrien-3,16α,17β-triol | 0.0 |
| 1,3,5[10]-Estratrien-3,17β-diol | 0.0 |
| 1,3,5[10]-Estratrien-3-ol-17-one | 0.0 |
| ISOTYPE (IgG1,2b; lambda light chain) | 1,2b |
| AFFINITY ($K_a$, L/mole × $10^{11}$) | 2.0 |

Direct ELISA for 16OHE1-Glucuronide Fraction in Urine

Polystyrene microtiter plates (96 well, C96 Maxisorb plate, NUNC, Napierville, Ill. USA) were coated with 100 μL/well, 1.5 μg/mL affinity purified rabbit anti-mouse IgG, Fc-fragment specific antibody (Jackson Immunoresearch, West Grove Pa. USA) in PBS and incubated overnight at room temperature. The plates were washed with PBS, blocked with 0.5% casein (w/v) in PBS, and stored wet until use. Assay Standards were prepared by serial dilution of 16OHE1-3-glucuronide in steroid-free human urine at concentrations ranging from 0.3 to 20 ng/mL. Preparation of steroid-free urine by charcoal-extraction is a well established procedure in the diagnostic arts.

For the assay, 10 uL of urine, Standards, and Positive and Negative Controls were aliquoted in triplicate into an 8×12 array of racked 1.2 mL microtubes (CalCon Incorporated, Claremont, Calif. USA). Microtubes are arranged in a pattern congruous with that of the ELISA plate assay wells such that liquid may be transferred directly from tubes to the assay well with an eight-channel pipettor. Sample aliquots were diluted 1:20 (v/v) by addition of 190 μL of 0.05M 2-[Morpholino]ethane sulfonic acid (MES) buffered saline (MESBS), pH 6.5, 2 mM EGTA, 5 mM ascorbic acid, 50 ng/mL dehydrotestosterone (DHT) containing 5 ng/mL of purified monoclonal antibody (Sample Diluent). Diluted urine samples were covered and incubated at room temperature for one hour. Seventy-five μL of Standards, Controls, and unknowns similarly diluted and incubated with Sample Diluent were transferred to wells of the washed rabbit anti-mouse IgG Fc antibody-coated microtiter ELISA plate with an eight-channel pipettor. To these wells was then added an additional 75 uL of a 1:2000 dilution (v/v) of 16OHE1-labeled alkaline phosphatase (300 U/mL) in Tris-buffered saline, pH 6.9, (TBS) containing 0.2% bovine gelatin (Conjugate Diluent), and plates were covered and incubated three hours at room temperature (20 deg C.). Plates were washed six times with TBS containing 0.05% Tween-20, and 100 μL of AP Enzyme Substrate containing 2 mM paranitrophenol phosphate (pNPP) in 1M diethanolamine was added to quantify 2MeoE1-labeled AP bound to the plate. Absorbance at 405 nm was read with an automated ELISA plate reader after 30 minutes. The concentration of said 2MeoE1-glucuronide fraction in unknowns was determined by reference and extrapolation from the standard curve using a four-parameter logistic curve fitting program (Kineti-Calc, Biotek Instruments, Wynooski, Vt. USA). In one variant of this assay, β-Glucuronidase (1000 U/mL, E. Coli) is added to the Sample Diluent, and the assay performed exactly as above. In this case, unconjugated 16OHE1 is used as Standard.

Direct ELISA for said 2MeoE1-Glucuronide Fraction in Urine

Polystyrene microtiter plates (96 well, C96 Maxisorb plate, NUNC, Napierville, Ill. USA) were coated with 100 μL/well, 1.5 μg/mL affinity purified rabbit anti-mouse IgG, Fc-fragment specific antibody (Jackson Immunoresearch, West Grove Pa. USA) in PBS and incubated overnight at room temperature. The plates were washed with PBS, blocked with 0.5% casein (w/v) in PBS, and stored wet until use. Assay Standards were prepared by serial dilution of 2MeoE1-3-glucuronide in steroid-free human urine at concentrations ranging from 0.3 to 20 ng/mL.

For assay, 10 μL of urines, Standards, and Positive and Negative Controls were aliquoted in triplicate into an 8×12 array of racked 1.2 mL microtubes (CalCon Incorporated, Claremont, Calif. USA). Microtubes are arranged in a pattern congruous with that of the ELISA plate assay wells such that liquid may be transferred directly from tubes to the assay well with an eight-channel pipettor. Sample aliquots were diluted 1:20 (v/v) by addition of 190 μL of 0.05M 2-[Morpholino]ethane sulfonic acid (MES) buffered saline (MESBS), pH 6.5, 2 mM EGTA, 5 mM ascorbic acid, 50 ng/mL dehydrotestosterone (DHT) containing 5 ng/mL of purified monoclonal antibody (Sample Diluent). Diluted urine samples were covered and incubated at room temperature for one hour. Seventy-five uL of Standards, Controls, and unknowns similarly diluted and incubated with Sample Diluent were transferred to wells of the washed rabbit anti-mouse IgG Fc antibody-coated microtiter ELISA plate with an eight-channel pipettor. To these wells was then added an additional 75 μL of a 1:2000 dilution (v/v) of 2MeoE1-labeled alkaline phosphatase (300 U/mL) in Tris-buffered saline, pH 6.9, (TBS) containing 0.2% bovine gelatin (Conjugate Diluent), and plates were covered and incubated three hours at room temperature (20 deg C.). Plates were washed six times with TBS containing 0.05% Tween-20, and 100 uL of AP Enzyme Substrate containing 2 mM paranitrophenol phosphate (pNPP) in 1M diethanolamine. was added to quantify 16OHE1-labeled AP bound to the plate. Absorbance at 405 nm was read with an automated ELISA plate reader after 30 minutes. The concentration of the 16OHE1-glucuronide fraction in unknowns was determined by reference and extrapolation from the standard curve using a four-parameter logistic curve fitting program (Kineti-Calc, Biotek Instruments, Wynooski, Vt. USA). In one variant of this assay, β-Glucuronidase (1000 U/mL, $E.\ Coli$) is added to the Sample Diluent, and the assay performed exactly as above. In this case, unconjugated 2MeoE1 is used as Standard.

Direct ELISA for said 2OHE1-Glucuronide Fraction in Urine

Polystyrene microtiter plates (96 well, C96 Maxisorb plate, NUNC, Napierville, Ill. USA) were coated with 100 μL/well, 1.5 μg/mL affinity purified rabbit anti-mouse IgG, Fc-fragment specific antibody (Jackson Immunoresearch, West Grove Pa. USA) in PBS and incubated overnight at room temperature. The plates were washed with PBS, blocked with 0.5% casein (w/v) in PBS, and stored wet until use. Assay Standards were prepared by serial dilution of 2OHE1-3-glucuronide in steroid-free human urine at concentrations ranging from 0.3 to 20 ng/mL.

For assay, 10 μL of urine, Standards, and Positive and Negative Controls were aliquoted in triplicate into an 8×12 array of racked 1.2 mL microtubes (CalCon Incorporated, Claremont, Calif. USA). Microtubes are arranged in a pattern congruous with that of the ELISA plate assay wells such that liquid may be transferred directly from tubes to the assay well with an eight-channel pipettor. Sample aliquots were diluted 1:20 (v/v) by addition of 190 μL of 0.05M 2-[Morpholino]ethane sulfonic acid (MES) buffered saline (MESBS), pH 6.5, 2 mM EGTA, 5 mM ascorbic acid, 50 ng/mL dehydrotestosterone (DHT) containing 5 ng/mL of purified monoclonal antibody (Sample Diluent). Diluted urine samples were covered and incubated at room temperature for one hour. Seventy-five μL of Standards, Controls, and unknowns similarly diluted and incubated with Sample Diluent were transferred to wells of the washed rabbit anti-mouse IgG Fc antibody-coated microtiter ELISA plate with an eight-channel pipettor. To these wells was then added an additional 75 μL of a 1:2000 dilution (v/v) of 2OHE1-labeled alkaline phosphatase (300 U/mL) in Tris-buffered saline, pH 6.9, (TBS) containing 0.2% bovine gelatin (Conjugate Diluent), and plates were covered and incubated three hours at room temperature (20 deg C.). Plates were washed six times with TBS containing 0.05% Tween-20, and 100 uL of AP Enzyme Substrate containing 2 mM paranitrophenol phosphate (pNPP) in 1M diethanolamine. was added to quantify 2MEOE$_1$ labeled AP bound to the plate. Absorbance at 405 nm was read with an automated ELISA plate reader after 30 minutes. The concentration of said 2MEOE$_1$ glucuronide fraction in unknowns was determined by reference and extrapolation from the standard curve using a four-parameter logistic curve fitting program (Kineti-Calc, Biotek Instruments, Wynooski, Vt. USA). In one variant of this assay, β-Glucuronidase (1000 U/mL, $E.\ Coli$) is added to the Sample Diluent, and the assay performed exactly as above. In this case, unconjugated 2OHE1 is used as Standard.

Direct ELISA for said 16OHE1-Glucuronide Fraction in Serum

Polystyrene microtiter plates (96 well, C96 Maxisorb plate, NUNC, Napierville, Ill. USA) were coated with 200 ng/well affinity purified rabbit anti-mouse IgG, Fc-fragment specific antibody (Jackson Immunoresearch, West Grove Pa. USA) in PBS and incubated overnight at room temperature. The plates were washed with PBS, blocked with 0.5% casein (w/v) in PBS, and stored wet until use. Assay Standards were prepared by serial dilution of 16OHE1-3-glucuronide in steroid-free (charcoal-extracted) human serum at concentrations ranging from 7.8 to 1000 pg/mL. Preparation of charcoal-extracted serum is a well established procedure in the diagnostic arts.

For assay, twenty-five uL of serum, Standards, and Positive and Negative Controls were aliquoted in duplicate into an 8×12 array of racked 1.2 mL microtubes (CalCon Incorporated, Claremont, Calif. USA). Microtubes are arranged in a pattern congruous with that of the ELISA plate assay wells such that liquid may be transferred directly from tubes to the assay well with an eight-channel pipettor. Sample aliquots were diluted 1:7 (v/v) by addition of 150 μL of 0.05M 2-[Morpholino]ethane sulfonic acid (MES) buffered saline (MESBS), pH 6.5, 2 mM EGTA, 5 mM ascorbic acid, 50 ng/mL dehydrotestosterone (DHT) containing 3 ng/mL of purified monoclonal antibody (Sample Diluent). Diluted sera samples were covered and incubated at 38 deg C. in a water bath for one hour. After cooling for 15 minutes, 75 μL of standards, controls, and unknowns were transferred to wells of a washed rabbit anti-mouse IgG Fc antibody-coated microtiter ELISA plate with an eight-channel pipettor. To these wells was then added and additional 75 μL of a 1:2000 dilution (v/v) of 16OHE1-labeled AP (300 U/mL) in Tris-buffered saline, pH 6.9, (TBS) containing 0.1% gelatin, pH 6.5 (Conjugate Diluent), and plates were covered and incubated overnight at 4 deg C. Plates were washed six times with TBS containing 0.05% Tween-20, and 150 μL of AP Enzyme Substrate containing 2 mM paranitrophenol phosphate (pNPP) in 1M diethanolamine was added to quantify 16OHE1-labeled AP bound to the plate. Absorbance at 450 nm was read with an automated ELISA plate reader after 30 minutes. The concentration of said 16OHE1-glucuronide fraction in unknowns was determined by reference and extrapolation from the standard curve using a four-parameter logistic curve fitting program (Kineti-Calc, Biotek Instruments, Wynooski, Vt. USA).

Direct ELISA for Total 16OHE1-Glucuronides in Serum

The assay for total 16OHE1-glucuronides in serum is done exactly as described above, except that all 16OHE1-glucuronides, both 3- and 16-glucuronides are deconjugated, that is, the glucuronides removed from estrogens in serum, prior to performing the ELISA. Standards for this assay are prepared by serial dilution of 16OHE1 in charcoal-extracted serum at 7.8 to 1000 pg/mL. Cleavage of steroidal glucuronides is achieved by incubation with the enzyme β-glucuronidase, preferably that isolated from the bacteria, *E. Coli*. In practice, *E. Coli* β-glucuronidase (Sigma Chemical Company, St. Louis Mo. USA), 1000 U/mL, is added to the MESBS serum dilution buffer, and the assay performed exactly as described above for Direct ELISA for 16OHE1-3-glucuronide Fraction. By this modification of a preferred assay of this invention, concentrations detected and/or quantified by direct ELISA with antibodies of this invention will be equal to or greater than those found by direct ELISA for said 16OHE1-glucuronide fraction (no deconjugation).

Each of the two direct ELISA formats described above, when utilized with monoclonal antibodies described above, will find greatest use in various situations. For example, the direct ELISA for said 16OHE1-glucuronide fraction is preferable when used for the diagnosis/prognosis of urinary metabolites. Different enzyme pretreatment of 16OHE1 metabolites in body fluids, such as serum, may be required to optimally liberate the sequestered 16OHE1-glucuronide fraction and thereby allow detection by the antibody.

APAAP Immunocytochemical Assay for 16OHE1-glucuronide Fraction in Tissue Sections Sections of 5 to 10 micron thickness cut from paraformaldehyde-fixed, paraffin-embedded tissues with a microtome are mounted on dry glass slides previously treated with 5% swine serum in PBS. Slides are heated at 60° C. for 30 minutes and dewaxed by immersion in xylene for 5 minutes. Tissue sections on slides are rehydrated by repetitive immersion in a graded series of ethanol/water solutions: 100% ethanol (3 min.); 95% ethanol (3 min.); 70% ethanol (3 min); and, finally, PBS (2×3 min.). Rehydrated tissues are immediately overlaid and incubated with 100 μL of monoclonal antibody at 5 μg/mL in TBS (Anti-16OHE1 Antibody Solution) for 30 minutes at room temperature. Slides are then washed by immersion in TBS (6×3 min) to remove antibody not bound to said 16OHE1-glucuronide fraction in tissue sections. One hundred μL of a solution containing polyclonal rabbit anti-mouse IgG Antibody Bridging Solution (DAKO Corporation, Carpenteria Calif. USA) in PBS is overlaid onto each tissue section, and incubated for 1 hour at room temperature. Slides with tissues are washed as in the previous step and tissues overlaid with a 100 uL aliquot of alkaline phosphatase: anti-alkaline phosphatase (APAAP Complex) (DAKO) in TBS for 30 minutes. The optimal dilution of anti-mouse IgG antisera (Antibody Bridging Solution) and APAAP Complex should be determined by titration, but should be about 1:25 in TBS, pH 7.4. After washing, tissues are incubated with 100 μL of naphthol phosphate (AS-MX)/Fast Red Enzyme Substrate for 10 min. The enzyme substrate is prepared by dissolving 2 mg naphthol AS-MX phosphate (Sigma Chemical Company, St. Louis Mo. USA) in 0.2 mL of NO-dimethyl formamide in a glass tube, and adding 10 mL of 0.1 M TBS, pH 8.2 (Enzyme Substrate Solution). Immediately before use, Fast Red hTR salt (Sigma) is dissolved at 12 mg/mL in the naphthol AS-MX solution and applied to the washed slides. Endogenous alkaline phosphatase activity in the mammalian tissues may be inhibited by adding 1 mM levamisole (Sigma) to the later solution. After an intense red color develops, the substrate is washed from the slide with water, and after blotting excess liquid, the tissues are preserved on the slides by mounting with glycerol vinyl alcohol solution (GVA Mount, Zymed, San Francisco, Calif. USA) and coverslipped for permanent storage.

Direct ELISA for said 2OHE1-glucuronide Fraction in Serum

The assay is done in a manner very similar to that for 16OHE1-glucuronide fraction (above). Polystyrene microtiter plates were coated with affinity purified rabbit anti-mouse IgG, Fc-fragment specific antibody in PBS and incubated overnight at room temperature. The plates are washed with PBS, blocked with 0.5% casein (w/v) in PBS, and stored wet until use. Assay Standards were prepared by serial dilution of 2OHE1-3-glucuronide in steroid-free (charcoal-extracted) human serum at concentrations ranging from 7.8 to 1000 pg/mL.

For the assay, twenty-five μL of serum, Standards, and Positive and Negative Controls are aliquoted in duplicate into an 8×12 array of racked 1.2 mL microtubes. Sample aliquots are diluted 1:7 (v/v) by addition of 150 uL of 0.05M 2-[Morpholino]ethane sulfonic acid (MES) buffered saline (MESBS), pH 6.5, with EGTA and ascorbate (as above) containing 3 ng/mL of purified monoclonal antibody (Sample Diluent). Diluted sera samples are covered and incubated at 38° C. in a water bath for one hour. After cooling for 15 minutes, 75 μL of standards, controls, and unknowns were transferred to wells of a washed rabbit anti-mouse IgG Fc antibody-coated microtiter ELISA plate. To these wells was then added and additional 75 μL of a 1:2000 dilution (v/v) of 2OHE1-labeled AP (300 U/mL) in TBS containing 0. 1% gelatin, pH 6.9 (Conjugate Diluent), and plates are covered and incubated overnight at 4 deg C. Plates are washed six times with TBS containing 0.05% Tween-20, and 150 μL of AP Enzyme Substrate pNPP is added to quantify 2OHE1-labeled AP bound to the plate. Absorbance at 450 nm is read after 30 minutes with an automated ELISA plate reader. The concentration of said 2OHE1-glucuronide fraction in unknowns was determined by reference and extrapolation from the standard curve.

Direct ELISA for Total 2OHE1, 2OHE2, and 2OHE3-Glucuronides in Serum

The assay for total 2-hydroxylated estrogen glucuronides in serum is conducted as described for 2OHE1-glucuronides above, except that all 2-hydroxylated-glucuronides, including 2OHE2- and 2OHE3-glucuronides are deconjugated, that is, the glucuronides removed from estrogens in serum, prior to performing the ELISA. This is possible because Mab 4C11, and similar antibodies, will recognize all unconjugated 2-hydroxylated estrogens, not just the 2OHE1. Standards for this assay are prepared by serial dilution of 2OHE1 in charcoal-extracted serum at 7.8 to 1000 pg/mL. Cleavage of steroidal glucuronides in serum is achieved by incubation with the enzyme β-glucuronidase, preferably that isolated from the bacteria, *E. Coli*. In practice, *E. Coli* β-glucuronidase, 1000 U/mL, is added to the MESBS serum dilution buffer, and the assay performed exactly as described above for Direct ELISA for 2OHE1-3-glucuronide Fraction. By this modification of the preferred assay of this invention, concentrations detected and/or quantified by direct ELISA with antibodies of this invention will be generally equal to or greater than those found by direct ELISA for said 2OHE1-glucuronide fraction (no deconjugation).

Each of the two direct ELISA formats described above, when utilized with monoclonal antibodies described above, will find greatest use in various situations. For example, the direct (no deconjugation) ELISA for said 2OHE1-glucuronide fraction is preferable when used for urinary metabolites. Different enzyme pretreatments of 2OHE1 metabolites in body fluids, such as in serum, may be required to release the sequestered glucuronide fraction for detection to allow detection by antibody.

APAAP Immunocytochemical Assay for 2OHE1-glucuronide Fraction in Tissue Sections This method follows that for immunocytochemical detection for 16OHE1 glucuronide described herein above. Sections of 5 to 10 micron thickness cut from paraformaldehyde-fixed, paraffin-embedded tissues with a microtome are mounted on dry glass slides previously treated with 5% swine serum in PBS. Slides are heated at 60° C. for 30 minutes and dewaxed immersion in xylene for 5 minutes. Tissues sections on slides are rehydrated by repetitive immersion in a graded series of ethanol/water solutions: 100% ethanol (3 min.); 95% ethanol (3 min.); 70% ethanol (3 min); and, finally, PBS (2×3 min.). Rehydrated tissues are immediately overlaid and incubated with 100 μL of monoclonal antibody at 20 μg/mL in TBS (Anti-2OHE1 Antibody Solution) for 30 minutes at room temperature. Slides are then washed by immersion in TBS (6×3 minutes) to remove antibody not bound to said 2OHE1-glucuronide fraction in tissue sections. One hundred μL of a solution containing polyclonal rabbit anti-mouse IgG Antibody Bridging Solution in PBS is overlaid onto each tissue section, and incubated for 1 hr at room temperature. Slides with tissues are washed as in the previous step and tissues overlaid with a 100 μL aliquot of alkaline phosphatase:anti-alkaline phosphatase (APAAP Complex) in TBS for 30 minutes. After washing, tissues are incubated with 100 μL of naphthol AS-MX/Fast Red Enzyme Substrate for 10 min. The enzyme substrate is prepared by dissolving 2 mg naphthol AS-MX phosphate (Sigma Chemical Company, St. Louis, Mo. USA) in 0.2 mL of NO-dimethyl formamide in a glass tube, and adding 10 mL of 0.1 M TBS, pH 8.2 (Enzyme Substrate Solution). Immediately before use, Fast Red TR salt (Sigma) is dissolved at 12 mg/mL in the naphthol AS-MX solution and applied to the washed slides. Endogenous alkaline phosphatase activity in the mammalian tissues may be inhibited by adding 1 mM levamisole (Sigma) to the later solution. After an intense red color develops, substrate is washed from the slide with water, and after blotting excess liquid, the tissues are preserved on the slides by mounting with glycerol vinyl alcohol solution and coverslipped for permanent storage.

Direct ELISAs for 2MeoE1-Glucuronide Fraction in Serum

The assay for 2MeoE1-glucuronide fraction in serum is conducted as described above for 16OHE1-glucuronide fraction, except that antibody to 2MeoE1 (9D3), 5 ng/mL, is used with 2MeoE1-labeled-AP (1:2000). Standards for this assay are prepared by serial dilution of 2MeoE1-3-glucuronide in charcoal-extracted serum at 7.8 to 1000 pg/mL.

Direct ELISA for Total 2-Methoxylated 2OHE1-, 2OHE2-, and 2OHE3-Glucuronide Fractions in Serum The assay for total 2-methoxylated 2-hydroxyestrogen glucuronides in serum is conducted as described for 2MeoE1-glucuronides above, except that all 2-methoxylated-glucuronides, including 2MeoE1-, 2MeoE2- and 2MeoE3-glucuronides are deconjugated, that is, the glucuronides removed from estrogens in serum, prior to performing the ELISA. This is possible because Mab 9D3 recognizes all unconjugated 2-methoxylated estrogens, not just the 2MeoE1. Standards for this assay are prepared by serial dilution of 2MeoE1 in charcoal-extracted serum at 7.8 to 1000 pg/mL. Cleavage of steroidal glucuronides in serum is achieved by incubation with the enzyme β-glucuronidase, preferably that isolated from the bacteria, *E. Coli*. In practice, *E. Coli* β-glucuronidase, 1000 U/mL, is added to the MESBS serum dilution buffer, and the assay performed exactly as described above for direct ELISA for 2MeoE1-3-Glucuronide Fraction. By this modification of the preferred assay of this invention, concentrations detected and/or quantified by direct ELISA with antibodies of this invention will be equal to or greater than those found by direct ELISA for said 2MeoE1-glucuronide fraction (no deconjugation). This assay format, in fact, measures the sum of 2MeoE1, 2MeoE2 (2-methoxyestradiol), and 2MeoE3 (2-Methoxyestriol) glucuronide fractions, and is, therefore, also an assay for this fraction in serum.

Each of the two direct ELISA formats described above, when utilized with monoclonal antibodies described above, will find greatest use in various situations, some described in the following examples.

ESTROGEN METABOLISM IN PERIMENOPAUSAL WOMEN: A LONGITUDINAL STUDY

In order to test the hypothesis that women developing osteoporosis have altered estrogen metabolism relative to women with normal bone mineral metabolism, a study of estrogen metabolism in perimenopausal and postmenopausal women between the ages of 48 and 57 years was designed. This age group was chosen because it is a this point in a women's life that the impact of estrogen in maintaining bone density is greatest; the average women loses between 1 and 8% of her bone mineral density (BMD) per year in the decade after natural menopause. Our goal was to longitudinally follow a population of women and distinguish them on the basis of BMD and rate of loss of BMD over a one year interval. We applied six basic criteria in deriving a sound experimental design: 1) inclusion of patient groups which are believed to most likely demonstrate the hypothesized effect, i.e., yield highest rate of "true positives" (fast bone losers); 2) inclusion of subjects most representative of the population as a whole; 3) Recruit subjects prospectively under set protocols to minimize confounding factors; 4) perform all tests on all patients at the same point in their clinical courses; 5) determine the "true" answers to clinical questions posed through independent test methods by comparison to that by the "gold" standard; and, 6) compare test results with the reference "gold" standard method by accepted statistical techniques. A well-designed study which meets all of these criteria was designed. The prevalence of rapid bone-loss in perimenopausal women (ages 48–57) may be as high as 20% (criteria 2 and 4). Actual bone density may be determined within 1% of actual by DEXA, affording an excellent "gold" standard for comparison with estrogen metabolism (criterion 5). Moreover, bone loss may be estimated from a single DEXA measurement by comparison with an age-normalized standard "Z-Score", or by sequential DEXA over a 12 month period (criteria 6).

Study Subjects

Seventy-one (71) women between the ages of 48 and 57 years were recruited from the clinics of the Bone Health Program of Washington University, St. Louis, Mo. All women had not had a normal menses for at least one year prior to inclusion in this Study. Women with chronic life-threatening diseases, or women on medications known to affect estrogen metabolism, including thyroid hormone and estrogens, were excluded from the Study. Each woman was interviewed initially (Visit 1) at the Bone Health Program by a Study nurse, and each subject completed a comprehensive medical, family medical, and dietary history. A baseline DEXA (QDR-2000, Hologics) was performed for BMD at all vertebral (VBD)and femural bone density (FBD) sites, and serum and saliva were collected at this initial visit. Each subject brought a 24-hour urine collection to the initial visit, having received the container and instructions for collection before the first visit. Saliva, serum, and urine were processed and aliquoted immediately, and stored frozen at $-70°$ C. until analysis. Each women was seen again twice at six-month intervals (Visits 2 and 3), each bringing a 24-hour urine specimen, and providing a saliva and serum sample, and subjected to a DEXA analysis for all VBD and FBD sites.

The Descriptive Relational Database

As a means of describing the study population, a relational database was created which included the following physical and medical information for each study participant: age; height; weight; race; age at first menses; years since menopause (YSM); body mass index (BMI); waist-hip ratio (WHR); family history of osteoporosis; cigarettes/day; smoking history; ozs. alcohol/day; drinking history; list of drugs now using; history of estrogen use; etc. Biochemical data in the database included: urinary and serum calcium, SMA-12 values (serum); urinary and serum creatinine; urinary estrogen metabolite levels 2OHE1-, 2MeoE1-, 16OHE1-Glucuronide Fractions and sums thereof; serum estrogen metabolite levels 2OHE1-, 2MeoE1-, 16OHE1- Glucuronide Fractions and sums thereof; etc. Bone densities for each participant for eight (8) vertebral and femur bone sites were entered in the database including among others: spine anterior projection (VBD-AP); spine lateral projection, volume and density (VBD-Lat-vol, VBD-Lat-tot); spine total (VDB-Tot); Lumbar spine (L1–L4); trochanter of the hip (FBD-Tr); Ward's triangle (FBD-W); the neck of the femur (FBD-N); and proximal femur total (FBD-Tot). The Z-Scores for each projection were also incorporated into the database.

The rates of yearly bone loss (or gain) for each VBD and FBD projection and corresponding Z-Scores of each participant were also included. Rates of BMD loss were calculated as the slope of the regression line interpolating three BMD measurements in one year, Data Analysis and Statistics Univariate (simple regression) analysis was performed relating each of the estrogen metabolite levels, sums thereof (dependent variable), to each of the following independent variables: body mass index; smoking status; estrogen use; waist-hip ratio; DEXA scan results (baseline bone mass and rate of bone loss); race; and age, among others. Correlation coefficients were calculated between each hormonal variable and each continuous independent variable. Non-parametric tests such as the Mann-Whitney U Test or the Kruskal-Wallis test was used in analysis involving analysis of two or more groups.

Pearson Partial Correlation analysis was applied to the entire population to explore the contribution of variables to BMD or changes in BMD. Besides estrogen metabolites, variables that are known to affect either bone density or estrogen metabolism, and those that were found to be correlated with bone density by simple correlation were included in the multivariate regression model; these included BMI, alkaline phosphatase, urinary calcium levels, past history of smoking, use of oral contraceptives, and family history of osteoporosis. Under this model, bone density (BD) is assumed to be a function of all of these variables, and the partial contribution of estrogen metabolites to bone densities may be calculated. Thus, $$BD^2 = \text{constant} + a^2(BMI)^2 + b^2(\text{alk.phos})^2 + \ldots + g^2(2OHE1)^2 + h^2(16OHE1)^2 + \ldots, \text{etc.},$$

where BD=VBD-L, or VBD-AP, or FBD-tot, etc., and the lower case letters refer to correlation coefficients. The General Linear Models (GLM) procedure handles variables that have discrete levels as well as continuous variables.

EXAMPLE 1

Relationship Between Urinary Metabolites and Bone Mineral Density in Perimenopausal Women The characteristics of the Study population are given in Table 4. Seventy-one healthy postmenopausal women (age 47–59 yr), never treated with drugs that affect bone or estrogen metabolism were initially enrolled in the Longitudinal Study. The data in Table 4. represents the baseline results of a one-year longitudinal observational study on the relationship between estrogen metabolism and bone density changes.

Bone density as a function of estrogen metabolism as indicated from measurement of urinary metabolites for this study group is illustrated in Table 5. Vertebral bone density (VBD), Lateral (VBD-L) and Antero-Posterior (VBD-AP) projections, as well as proximal femur bone density, Neck (FBD-N), Trochanter (FBD-Tr); Ward's (FBD-W), and Total (FBD-Tot) were measured by Dual Energy X-ray Absorptiometry (QDR-2000, Hologic). Simple linear regression indicated that 2MeoE1- and 2OHE1-glucuronide fractions were significantly negatively correlated with VBD and FBD, whereas 16OHE1-glucuronide fraction was weakly, but significantly, negatively correlated with FBD at most areas. The most significant correlation was between urinary 2MeoE1/Cr and BMD at femoral bone sites, particularly the trochanter, where r=−0.44, and p<0.0002.

Pearson Partial Correlation analysis was applied to the entire population. Besides estrogen metabolites, variables that are known to affect either bone density of estrogen metabolism, and those that were found to be correlated with bone density by simple correlation were included in the multivariate regression model. Under this model, bone density (BD) is assumed to be a function of all of these variables, and the partial contribution of estrogen metabolites to bone densities may be calculated. The partial correlations under this model are given in Table 6. After correction for possible confounders, urine estrogen metabolites were still significantly correlated with VBD-L, whereas the correlation between FBD and 2OHE1 was lost, and that with 16OHE1 became weaker. In addition, 2OHE1, but not 16OHE1, was independently and positively correlated with YSM (partial r=+0.33 ) (Years Since Menopause, data not shown), years of use of oral contraceptives r=+0.21), and family history of osteoporosis (partial r=+0.23). BMI was significantly correlated with bone density at all sites (partial r>0.30).

Results of testing and analysis on Visit #2 and Visit #3 urines were in accord with that of Visit #1. There was no improvement of results if the results of all three Visits were averaged before statistical analysis.

Increased concentrations of urinary metabolites may arise from increased estrogen production or increased metabolic conversion, or both. To help resolve which of the former might explain the observations, we examined the simple correlations of urinary estrogen metabolites with changes in bone density ("delta" BMD) over a one year period. Simple correlations between the average (Visits 1, 2, 3) urinary metabolites, and the changes in bone densities at several BMD measurement sites in the Longitudinal Study Group were performed. No significant effects of urinary estrogen metabolites were observed on the rate of changes of proximal femur (FBD) and antero-posterior spine BMD (VBD-AP) (data not shown). The urinary metabolite 16OHE1, correlated positively, albeit weakly and not significantly, with changes in BMD of the lateral spine (VBD-L).

It is possible that perimenopausal women who are losing bone have a different estrogen metabolic pattern than women not losing bone. To explore this possibility, we examined the simple correlations between estrogen urinary metabolites and VBD/FBD in women who lost ("losers") or did not lose bone ("gainers") in that specific VBD or FBD DEXA measurement. There were 13 (N=13) women in the longitudinal group who lost greater than normal (>4–5%/year) amounts of bone density during the one year study. In sharp contrast to the results for the entire group, there are correlations between certain urinary metabolites and rate of change in certain bone densities in women rapidly losing bone ("losers"). For example, there are significant positive correlations between urinary 2OHE1/creatinine and 16OHE1/creatinine and the rate of change of BMD r=+0.75, $p<0.005$ r=+0.49, $p<0.04$, respectively), but only as estimated from changes in lateral spine BMD(delta VBD-L), and no other sites. We found no significant correlations between urinary estrogen metabolites in women not losing bone ("non-losers").

It is unlikely, therefore, that the levels of urinary estrogen metabolites can, by themselves, predict the rate of change in BMD in perimenopausal women. Women in early menopause are producing ovarian estrogen, estradiol, and estrogen from aromatization of androgens in peripheral tissues to form estrone. In early menopause, urinary estrogen levels are marking both estrogen production rate and peripheral metabolism. In middle and late postmenopause, however, the primary source of estrogen is from peripheral aromatization to form estrone. At that point, urinary metabolites may better predict the rate of bone loss.

The following conclusions may be drawn from testing and analysis of the Longitudinal Study data obtained from testing of urinary estrogen metabolites of perimenopausal women:

1. Low bone density in early postmenopausal women is associated with higher urinary excretion of active and inactive estrogen metabolites, predominantly the inactive estrogens, particularly 2MeoE1 glucuronide fraction.
2. Large body mass (BMI) may protect postmenopausal women from the negative effects of estrogen catabolism, in part by providing a relatively larger production of estrogen from androgens.
3. An increased 2-hydroxylation of estrone to inactive metabolites may contribute to a low or decreasing bone density during menopause, and represents an hereditary factor for estrogen-dependent osteoporosis.
4. Very rapid loss of bone density in early postmenopausal women, however, is associated with lower excretion of urinary inactive estrogen metabolites pointing to reduced production of estrogen in this group.
5. Increased 2-hydroxylation of estrogens contributes to decreased bone density before and during menopause, but rapid bone loss in peri- and post-menopausal women additionally reflects reduced availability of estrogen.
6. Increased availability of active estrogens, including 16OHE1, may protect vertebral density, whereas accentuated C-2 hydroxylation of estrogen to inactive metabolites is associated with low BMD.

TABLE 4

CHARACTERISTICS OF THE LONGITUDINAL STUDY POPULATION
(Baseline, Visit #1 of Study)

| | n | Mean ± SD | Range |
|---|---|---|---|
| AGE | 71 | 54 ± 3 | 47–59 |
| Years Since Menopause | 71 | 7 ± 6 | 1–27 |
| BMI (kg/m$^2$) | 71 | 26.9 ± 5.6 | 18.1–41.1 |
| Alkaline Phosphatase (IU/L) | 71 | 92 ± 32 | 36–223 |
| Urine Calcium (mg/g creat.) | 70 | 141 ± 95 | 27–550 |
| Oral Contraceptives (yrs used) | 70 | 4.4 ± 5.3 | 0–21 |
| Past Smoking (pack-years) | 71 | 5.4 ± 10.8 | 0–54 |
| VBD-AP (Z-Score) | 64 | −0.06 ± 1.09 | −2.31–+2.94 |
| VBD-L (Z-Score) | 64 | +0.11 ± 1.28 | −4.16–+3.20 |
| VBD-L volummetric (g/cm$^3$) | 64 | 0.198 ± 0.033 | 0.088–0.289 |
| Neck (Z-Score) | 71 | −0.32 ± 0.90 | −2.28–+1.48 |
| Trochanter (Z-Score) | 71 | −0.24 ± 0.98 | −2.28–+2.15 |
| Ward (Z-Score) | 71 | +0.16 ± 1.12 | −2.36–+3.30 |
| Total (Z-Score) | 71 | −0.39 ± 0.87 | −1.99–+1.31 |
| 2-Methoxyestrone (ug/g creat) | 70 | 1.35 ± 0.84 | 0.35–4.40 |
| 2-Hydroxyestrone (ug/g creat) | 70 | 6.21 ± 4.98 | 0.34–38.4 |
| 16α-Hydroxyestrone (ug/g creat) | 70 | 2.66 ± 1.81 | 0.44–9.29 |
| Estriol (ug/g creat) | 69 | 5.98 ± 3.77 | 1.07–23.2 |

TABLE 5

BONE DENSITY AS A FUNCTION OF ESTROGEN METABOLISM
(Longitudinal Study, Visit #1 urinary metabolites)

Simple Correlations

| | VBD-L | VBD-Lv | VBD-AP | VBD-N | FBD-Tr | FBD-W | FBD-Tot |
|---|---|---|---|---|---|---|---|
| n | 63 | 63 | 70 | 70 | 70 | 70 | 70 |
| 2MeoE1 | −0.36** | −0.37** | −0.29* | −.028* | −0.44*** | −0.26* | −0.43*** |

TABLE 5-continued

BONE DENSITY AS A FUNCTION OF ESTROGEN METABOLISM
(Longitudinal Study, Visit #1 urinary metabolites)

Simple Correlations

|        | VBD-L  | VBD-Lv | VBD-AP | VBD-N | FBD-Tr  | FBD-W | FBD-Tot |
|--------|--------|--------|--------|-------|---------|-------|---------|
| 2OHE1  | −0.25* | −0.30* | <0.10  | −0.20 | −0.34** | −0.23 | −0.33** |
| 16OHE1 | −0.23  | −0.24  | −0.22  | −0.21 | −0.29*  | −0.20 | −0.27*  |
| Estriol| −0.22  | −0.21  | <0.10  | −0.20 | −0.14   | −0.15 | −0.26   |

*denotes significance of $p < 0.05$; $p < 0.01$; *$p < 0.001$

TABLE 6

PARTIAL CORRELATIONS
(Longitudinal Study, Visit #1 urinary metabolites)

|           | VBD-L  | VBD-Lv | VBD-AP | FBD-N | FBD-Tr  | FBD-W | FBD-Tot |
|-----------|--------|--------|--------|-------|---------|-------|---------|
| n         | 63     | 63     | 70     | 70    | 70      | 70    | 70      |
| 2MeoE1    |        |        |        |       | −0.44** |       |         |
| 2OHE1     | −0.21  | −0.33* | +0.25  | <0.10 | −0.11   | −0.12 | <0.10   |
| 16OHE1    | −0.37* | −0.41* | <0.10  | −0.21 | −0.21   | −0.21 | −0.26   |
| Sum 2 + 16| −0.30  | −0.42* | −0.18  | −0.13 | −0.16   | −0.14 | −0.16   |
| Estriol (E3)| −0.13| −0.24  | +0.20  | −0.20 | −0.13   | −0.20 | −0.20   |

Values represent simple r; *denotes $p < 0.05$, **denotes $p < 0.01$.

EXAMPLE 2

Relationship Between Serum Metabolites and Bone Mineral Density in Perimenopausal Women The levels of estrogen metabolites in urine largely reflect the production of estrogen and the peripheral metabolism of produced estrogens (see Example 1, above). By contrast, the levels of estrogen metabolites within the circulating physiological fluids of a mammal should be a reflection of the biological availability of that metabolite to peripheral target tissues such as bone. Therefore, serum levels of estrogen metabolites in perimenopausal women (Longitudinal Study) may be a better predictor of endogenous estrogen exposure and hence correlate with bone density and the rate of change in bone density.

In order to test the later hypothesis, sera from women in the Longitudinal Study above (Example 1) were assayed for estrogen metabolites by methods of the present invention (see above). The Simple Correlations between levels of serum metabolites collected at Visit #2 and bone densities as estimated from DEXA analysis of various estimates of VBD and FBD are given in Table 7 below. Note that there is a significant negative correlation between levels of serum 2OHE1-glucuronide fraction (2OHE1) and bone density, whereas there is a positive correlation between levels of serum 16OHE1-glucuronide fraction and bone density. The most significant correlations are found between serum metabolites and total vertebral bone density (VBD-Tot), r=−0.24 for 2OHE1 ($p<0.05$), and r=+0.20 for 16OHE1 ($p<0.12$).

TABLE 7

Correlation between Bone Mineral Density and Estrogen Metabolite Levels in serum (Visit 2) of Perimenopausal Women in Longitudinal Study. Bone Densities estimated from DEXA at vertebral (VBD) and Femural (FBD) sites vs. serum estrogen glucoronide fraction concentrations measured by EIAs of the present invention.

| | SIMPLE CORRELATIONS (r) | | | |
|---|---|---|---|---|
| METABOLITE | VBD-Tot | FBD-Tr | VBD-L | VBD-AP |
| 2OHE1 | −0.24* | −0.16 | −0.16 | −0.03 |
| 16OHE1 | 0.20 † | 0.17 | 0.17 | 0.13 |

Levels of Significance †, $p < 0.12$; *, $p < 0.05$; **, $p < 0.01$.

Correlations between the rate of bone loss and serum estrogen metabolites levels in all perimenopausal women in the Longitudinal Study are given in Table 8. In contrast to the negative findings for the urinary metabolites, measurements of serum metabolites found very significant and consistent correlations between certain metabolites and the rate of bone loss in all perimenopausal women. For example, there is a negative correlation between serum 2OHE1-glucuronide fraction and rate of change in bone density at all vertebral and femural bone sites of DEXA analysis, most significantly at the lateral vertebral site where r=−0.38, and $p<0.004$. Similar negative and significant correlations were also found between 2MeoE1-glucuronide fraction and DEXA estimates of rate of bone loss. No significant correlations between rates of bone loss and serum 16OHE1-glucuronide fraction were found in this Study of perimenopausal women. However, positive correlations were found between serum 16OHE1 and rate of change in bone density suggesting that serum 16OHE1-glucuronide fraction will be a useful predictor for increasing BMD in certain instances.

The strength of the negative correlations between rates of bone loss and levels of 2-hydroxylated metabolites is greatest in women experiencing bone loss, and there is a dose effect. For example, Table 8. illustrates that at all vertebral sites, the correlation between rate of bone loss and serum 2OHE1-glucuronide fraction is strongest amongst women losing bone. This finding is likely due to the inability of DEXA to accurately detect changes in BMD over a one year period; a more accurate method would find better correlations for lesser changes in BMD.

TABLE 8

Correlations between Rate of Bone Density Loss and Estrogen Metabolite Levels in Serum (Visit 2) of Perimenopausal Women. Change in Bone Densities estimated from DEXA at vertebral (VBD) and femural (FBD) sites vs. serum estrogen glucuronide fraction concentrations measured by EIA.

SIMPLE CORRELATIONS (r) with VBD-AP

| METABOLITE | ALL (n = 64) | NON-LOSERS (n = 14) | LOSERS (n = 50) |
|---|---|---|---|
| 2OHE1 | −0.28* | 0.26 | −0.40** |
| 2MeoE1 | −0.14 | 0.004 | −0.27 |
| 2OHE1 + 2MeoE1 | −0.15 | 0.14 | −0.36** |

SIMPLE CORRELATIONS (r) with VBD-L

| METABOLITE | ALL (n = 52) | NON-LOSERS (n = 30) | LOSERS (n = 22) |
|---|---|---|---|
| 2OHE1 | −0.40** | −0.18 | −0.27 |
| 2MeoE1 | −0.33* | −0.15 | −0.36† |
| 2OHE1 + 2MeoE1 | −0.30* | — | −0.34 |

SIMPLE CORRELATIONS (r) with FBD-Tr

| METABOLITE | ALL (n = 60) | NON-LOSERS (n = 40) | LOSERS (n = 21) |
|---|---|---|---|
| 2OHE1 | −0.30 | −0.21 | −0.12 |
| 2MeoE1 | −0.23 | −0.15 | −0.13 |
| 2OHE1 + 2MeoE1 | −0.22† | −0.21 | −0.14 |

SIMPLE CORRELATIONS (r) with VBD-Tot

| METABOLITE | ALL (n = 62) | NON-LOSERS (n = 36) | LOSERS (n = 23) |
|---|---|---|---|
| 2OHE1 | −0.22† | −0.21 | −0.42* |
| 2MeoE1 | −0.21† | −0.15 | −0.49* |
| 2OHE1 + 2MeoE1 | −0.23† | −0.21 | −0.49* |

†indicates that significance of correlation is $p < 0.10$; *$p < 0.05$; and **$p < 0.010$.

EXAMPLE 3

The Clinical Utility of Urinary and Serum Estrogen Metabolite Assays in Detecting and Managing Osteopenic Pathologies The results and clinical data presented in Examples 1 and 2 above indicate that the assays of the present invention will find many uses in the medical diagnosis, monitoring, and treatment of osteopenic states, including osteoporosis.

By way of illustration, but not limitation, the assays of the present invention that detect urinary metabolites of estrone, particularly 2OHE1- and 2MeoE1-glucuronide fraction, most preferably 2MeoE1-glucuronide fraction, may be used to identify women that have low bone mineral density. In practice, a urine sample is collected and the concentration of 2MeoE1-glucuronide fraction determined. The concentration of urinary 2MeoE1 is normalized to levels of urinary creatinine (Ucr) or other estimates of renal clearance rate to correct for differences in urine volumes. The 2MeoE1/UCr ratio (e.g., micromole/mg) from that woman is compared to standardized, age-corrected urinary 2MeoE1/UCr ratios of women with known bone densities. If the 2MeoE1/UCr is significantly greater (+one standard deviation) than that of non-osteoporotic women of the same age, then the woman under testing has a high probability of having, or developing, osteoporosis. Such tests may be used in conjunction with DEXA analysis, or other tests, to determine the contribution of estrogen status to bone mineral density. This same assay can then be used in these women to monitor the effects of therapeutic treatments and/or dietary interventions on the metabolism of estrogens. A reduction in urinary 2MeoE1 would signal a shift in metabolism toward a state that would promote an increase in active estrogens and increasing bone density. The measurement of the levels of the metabolites in serum of women would serve a similar purpose, and provide a less expensive, safer, and earlier opportunity for detection and intervention than other methods such as DEXA.

Figure 5:
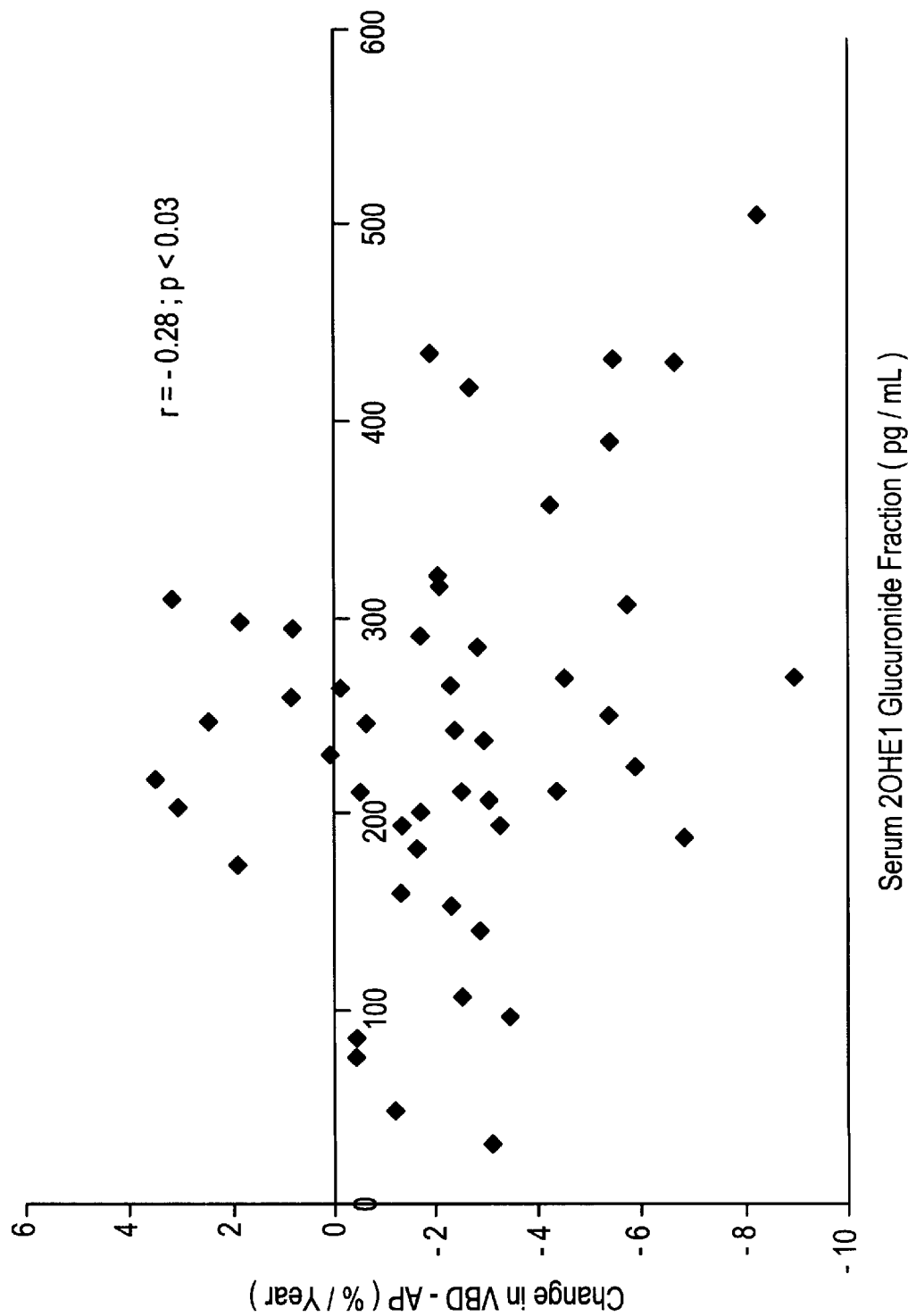
FIG. 5 is a plot of the yearly percent change in Vertebral Bone Density, Antero-posterior projection of DEXA (VBD-AP) versus Serum 2OHE1 in a group of perimenopausal women.
Figure 6:
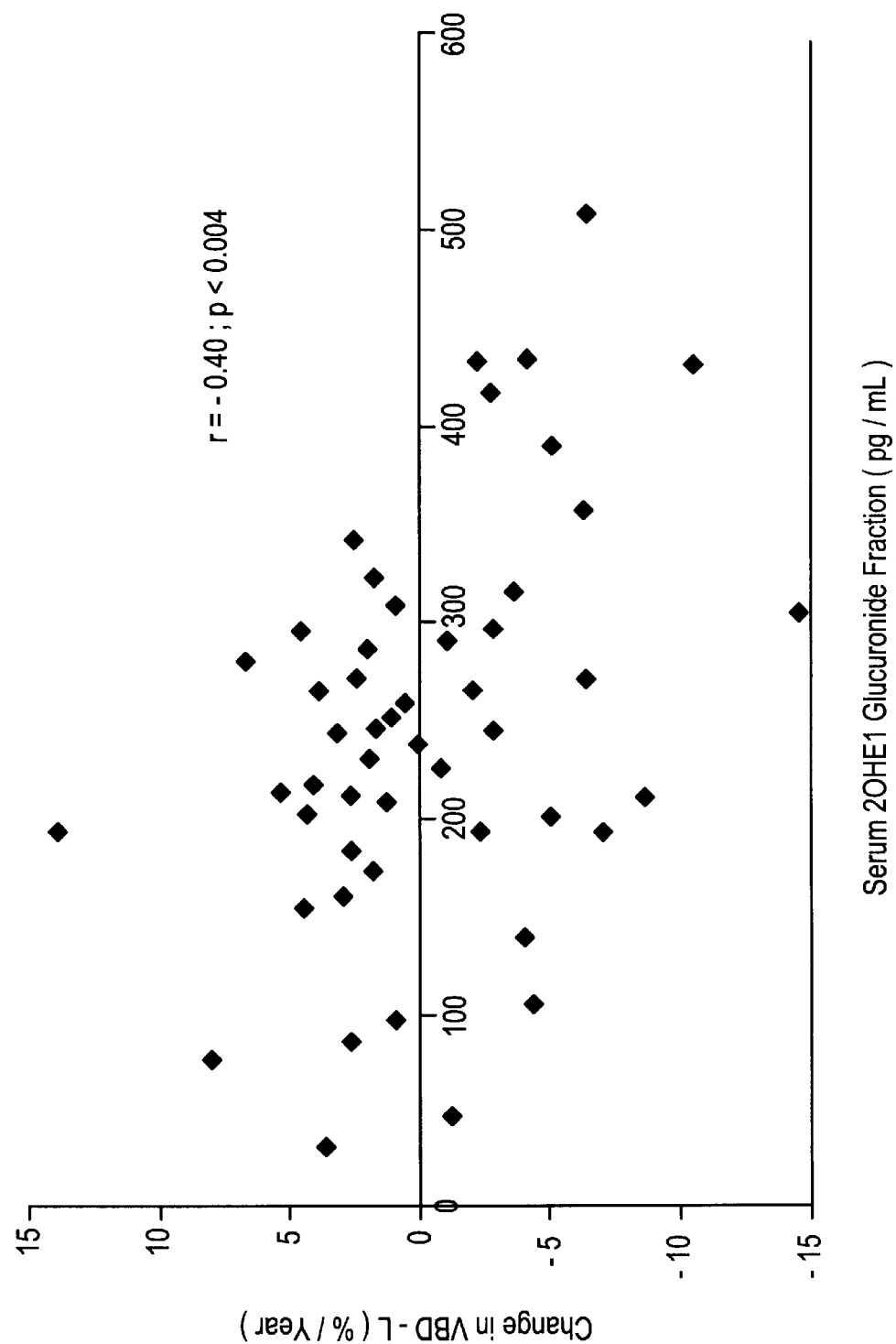
FIG. 6 is a plot showing the yearly change in Vertebral Bone Density, lateral projection (VBD-L) versus serum 2OHE1 in a group of perimenopausal women.

By way of illustration, but not limitation, the assays of the present invention that detect serum metabolites of estrone, most particularly 2OHE1- and 2MeoE1-glucuronide fraction, most preferably serum 2OHE1-glucuronide fraction, may be used to identify perimenopausal women that are experiencing a rapid loss of BMD. FIG. 5, illustrates one way in which the serum levels of 2OHE1-glucuronide fraction may be used to diagnose type I osteoporosis. FIG. 5. plots the rate of vertebral bone loss, anterior-posterior projection (VBD-AP), versus the levels of serum 2OHE1-glucuronide fraction in 60 perimenopausal women from the Longitudinal Study of Examples I and II above. The rate of change in VBD-AP correlates significantly with serum 2OHE1, with $r=−0.28$, and $p<0.03$. Note that all women with a serum 2OHE1-glucuronide fraction greater than 330 pg/mL cutoff (N=8) are experiencing bone loss, and of these 5 women have lost more than 5 percent of their BMD in one year. This represents about 45% of all women undergoing rapid bone loss (BMD change >−5%/year). Thus, this test could be used to detect Type I osteoporosis in perimenopausal women. In practice, a sample of serum or plasma from a woman would be tested for concentration of 2OHE1-glucuronide fraction by assays of the present invention. If the concentration of 2OHE1-glucuronide fraction were significantly greater (e.g., + one standard deviation) than "healthy", non-osteopenic women of the same age, then the woman under testing would have a high risk of having or development of osteoporosis. In addition, it would not require an undue amount of testing and experimentation to determine additional reference values for serum 2OHE1 or other 2-hydroxyestrogen that could be used to detect estrogen-related osteopenic states in premenopausal women, postmenopausal women, or men. As discussed earlier, urine or serum samples from premenopausal women could be normalized by collection at specific points within the menstrual cycle, preferably during the early preovulatory period. Moreover, other estimates of loss of BMD, such as changes in vertebral bone mineral density, lateral projection (VBD-L) may provide better selection of reference values for serum 2OHE1 or other serum estrone metabolite-glucuronide fractions. For example, FIG. 6. plots the rate of vertebral bone loss, lateral projection (VBD-L), versus the levels of serum 2OHE1-glucuronide fraction in 60 peri-menopausal women from the Longitudinal Study of Examples I and II above.

The rate of change in VBD-L correlates very significantly with serum 2OHE1, with $r=−0.40$, and $p<0.004$. Note that none of the women with serum 2OHE1-glucuronide fraction less than 175 pg/mL (N=10) are losing bone rapidly, whereas, all of women with 2OHE1 greater than 330 pg/mL (N=8) are losing bone, 4 women rapidly. This same assay can be used in these women to monitor the effects of therapeutic treatments and/or dietary interventions on the metabolism of estrogens. A reduction in serum 2OHE1 and/or an increase in serum 16OHE1 would signal a shift in metabolism toward a state that would promote an increase in active estrogens and increasing bone density.

EXAMPLE 4
ELISA Test Kit for 2OHE1-glucuronide Fraction in Serum

All materials and reagents to perform the ELISA for serum 2OHE1-glucuronide are preferably packaged together in a single kit. The kit includes an antibody-coated microtiter plate (anti-mouse IgG Fc-specific antibody), a microtube rack (96×1.2 mL tubes), two adhesive microtiter plate covers, Sample Diluent containing monoclonal antibody to 2OHE1-glucuronide fraction (21 mL), Enzyme Conjugate Diluent (10 mL), 2OHE1-labeled-alkaline phosphatase (AP) (20 ul in 0.5 mL vial), AP Enzyme Substrate (paranitrophenylphosphate, pNPP) (21 ml), 2OHE1-3-glucuronide Standards (25–800 pg/mL) in charcoal-extracted serum (6×300 ul/vial), Positive Controls (2×300 ul/vial), a Negative Control (300 ul/vial), and Instructions for use of the Kit. The kit will determine serum 2OHE1-glucuronide in thirty-two serum samples. Compositions of kit components are as described in Direct ELISA for said 2OHE1-glucuronide Fraction in Serum, above. ELISA kits for 16OHE1-glucuronide fraction, and 2MeoE1-glucuronide fraction in serum are fashion in a similar manner as the 2OHE1-glucuronide fraction kit. Compositions of kit components are as described in Direct ELISA for said 16OHE1-Glucuronide Fraction, and Direct Elisa for 2MeoE1- Glucuronide Fraction in Serum, above.

EXAMPLE 5
APAAP Immunocytochemical Test Kit for 2OHE1-glucuronide Fraction in Tissues All materials and reagents for immunostaining for 2OHE1-glucuronide fraction in fresh and/or paraffin-embedded fixed tissues may be brought together in a single kit. The kit includes 100 glass slide pretreated with swine serum, Anti-2OHE1 Antibody Solution (6 mL in dropper vial), Antibody Bridging Solution (6 mL in dropper vial), APAAP Complex (10 mL in dropper vial), Enzyme Substrate Solution (21 mL), 5 naphthol phosphate, Fast Red TR tablets, GVA Mount Solution (10 mL), TBS Wash and Dilution Buffer (5×30 mL, salts for reconstitution), and Instructions for use of the Kit. Negative and Positive Control Slides consisting of sectioned paraffin-embedded tissues mounted on swine serum-treated slides are included. Compositions of kit components are as described in APAAP Immunocytochemical Assay for 2OHE1-glucuronide Fraction in Tissue Sections, above. A similar kit may be prepared for tissue staining of 16OHE1-glucuronide fraction, and compositions and components are as described in APAAP Immunocytochemical Assay for 16OHE1-glucuronide Fraction in Tissue Sections, above. Each kit will enable staining of at least 50 tissue sections.

Various modifications of this invention in addition to those shown and described herein will become apparent to those in the art from the foregoing description. Such modifications are intended to be within the scope of the appended claims. The references herein cited are hereby incorporated by reference.

What is claimed is:

1. A method of screening for an osteopenic pathology affecting estrogen-sensitive tissues of a human wherein an altered level of a metabolite of estrone and its respective 3-glucuronide is indicative of the pathology, or a susceptibility thereto, in said human which comprises:

A. obtaining a urine, serum or tissue sample from said human in which said pathology is suspected;
   B. detecting the level of a particular metabolite of estrone and its respective 3-glucuronide from said sample;
   C. comparing this said level with the level derived from the testing of healthy humans to detect differences therefrom of said particular metabolite of estrone and its respective 3-glucuronide.

2. The method of claim 1 wherein said metabolites are selected from the group consisting of the products of enzymatic hydroxylation of estrone.

3. The method of claim 1 wherein said metabolites are selected from the group consisting of 2-hydroxyestrone, 16α-hydroxyestrone and 2-methoxyestrone.

4. The method of claim 1 wherein the 3-glucuronide is subjected to deconjugation to the free metabolite of estrone with the enzyme β-glucuronidase prior to analysis of tissue samples.

5. The method of claim 1 wherein said metabolite comprises 16α-hydroxyestrone and its 3-glucuronide.

6. The method of claim 1 wherein said metabolite comprises 2-hydroxyestrone and its 3-glucuronide.

7. The method of claim 1 wherein said metabolite comprises 2-methoxyestrone and its 3-glucuronide.

8. The method of claim 1 wherein said level is measured by immunochemical analysis.

9. The method of claim 8 wherein said immunochemical analysis is a competitive inhibition immunoassay.

10. The method of claim 9 wherein said immunochemical analysis is a competitive enzyme-linked immunoassay (ELISA) using monoclonal antibodies and 16α-hydroxyestrone (16OHE1)-enzyme conjugates which comprises:

(a) adding to a microtiter plate coated with monoclonal antibody specific for 16α-hydroxyestrone (16OHE1)-3-glucuronide a sample of patient serum mixed with an enzyme covalently labeled with 16α-hydroxyestrone (16OHE1),
   (b) incubating the mixture from (a) for a period of incubation permitting competition between 16α-hydroxyestrone (16OHE1)-enzyme and serum 16α-hydroxyestrone (16OHE1)-glucuronide fraction for binding to monoclonal antibody bound to a solid phase;
   (c) washing the plate;
   (d) adding to the washed plate a color-generating enzyme substrate to determine the amount of 16α-hydroxyestrone (16OHE1)-enzyme bound;
   (e) determining the quantity of 16α-hydroxyestrone (16OHE1) -glucuronide fraction in each serum sample from the absorbance of the sample relative to a set of 16α-hydroxyestrone (16OHE1)-glucuronide standards and controls of known concentration; and
   (f) comparing the level of the 16OHE1-glucuronide fraction in the serum sample to an extrinsic numerical value derived either previously from the patient under testing, or from the testing of other subjects of the same species, to detect any differences in the level of said estrone metabolite and its glucuronide standards previously determined to ascertain the presence of abnormal levels of 16OHE1-glucuronide fraction indicative of an osteopenic pathology.

11. The method of claim 10 wherein the assay is buffered so as to be kept acidic to protonate said glucuronide fraction, thereby minimizing charge interactions with proteins in tissues and body fluids.

12. The method of claim 10 wherein the assay is performed at 15 degrees Centigrade.

13. The method of claim 9 wherein said immonochemical analysis is a competitive enzyme-linked immunoassay (ELISA) using monoclonal antibodies and 2-hydroxyestrone (2OE1)-enzyme conjugates which comprises:
(a) adding to a microtiter plate coated with monoclonal antibody specific for 2-hydroxyestrone (2OE1)/2-hydroxyestrone (2OE1) 3-glucuronide a sample of patient serum mixed with an enzyme covalently labeled with 2-hydroxyestrone (2OE1),
b) incubating the mixture from (a) for a period of incubation permitting competition between 2-hydroxyestrone (2OE1)-enzyme and serum 2-hydroxyestrone (2OE1)-glucuronide fraction for binding to monoclonal antibody bound to a solid phase;
(c) washing the plate;
(d) adding to the washed plate a color-generating enzyme substrate to determine the amount of 2-hydroxyestrone (2OE1)-enzyme bound;
(e) determining the quantity of 2-hydroxyestrone (2OE1)-glucuronide fraction in each serum sample from the absorbance of the sample relative to a set of 2-hydroxyestrone (2OE1)-glucuronide standards and controls of known concentration; and
(f) comparing the level of the 2-hydroxyestrone (2OE1)-glucuronide fraction in the serum sample to an extrinsic numerical value derived either previously from the patient under testing, or from the testing of other subjects of the same species, to detect any differences in the level of said estrone metabolite and its glucuronide standards previously determined to ascertain the presence of abnormal levels of 2-hydroxyestrone (2OE1)-glucuronide fraction indicative of an osteopenic pathology.

14. The method of claim 13 wherein the assay is buffered so as to be kept acidic to protonate said glucuronide fraction, thereby minimizing charge interactions with proteins in tissues and body fluids.

15. The method of claim 13 wherein the assay is performed at 15 degrees Centigrade.

16. The method of claim 9 wherein said immunochemical analysis is a competitive enzyme-linked immunoassay (ELISA) using monoclonal antibodies and 2-methoxyestrone (2MeoE1)-enzyme conjugates which comprises:
(a) adding to a microtiter plate coated with monoclonal antibody specific for 2-methoxyestrone (2MeoE1)/2-methoxyestrone (2MeoE1)-3-glucuronide a sample of patient serum mixed with an enzyme covalently labeled with 2-methoxyestrone (2MeoE1);
(b) incubating the mixture from (a) for a period of incubation permitting competition between 2-methoxyestrone (2MeoE1)-enzyme and serum 2-methoxyestrone (2MeoE1)-glucuronide fraction for binding to monoclonal antibody bound to a solid phase;
(c) washing the plate;
(d) adding to the washed plate a color-generating enzyme substrate to determine the amount of 2MeoE1-enzyme bound;
(e) determining the quantity of 2MeoE1-glucuronide fraction in each serum sample from the absorbance of the sample relative to a set of 2MeoE1-glucuronide standards and controls of known concentration; and
(f) comparing the level of the 2MeoE1-glucuronide fraction in the serum sample to an extrinsic numerical value derived either previously from the patient under testing, or from the testing of other subjects of the same species, to detect any differences in the level of said estrone metabolite and its glucuronide standards previously determined to ascertain the presence of abnormal levels of 2MeoE1-glucuronide fraction indicative of an osteopenic pathology.

17. The method of claim 16 wherein the assay is buffered so as to be kept acidic to protonate said glucuronide fraction, thereby minimizing charge interactions with proteins in tissues and body fluids.

18. The method of claim 16 wherein the assay is performed at 15 degrees Centigrade.

19. The method of claim 1 wherein said level is measured in tissue.

20. The method of claim 19 wherein said level is measured by immunohistochemical detection.

21. The method of claim 20 wherein the method of immunohistochemical detection is by the alkaline phosphatase-anti-alkaline phosphatase (APAAP) method.

22. The method of claim 21 wherein the alkaline phosphatase-anti-alkaline phosphatase (APAAP) method comprises:
(a) incubating fixed tissue sections mounted on glass slides sequentially with:
1) mouse monoclonal antibody to said 16OHE1-glucuronide fraction; 2) rabbit polyclonal anti-mouse IgG antiserum, and 3) mouse anti-alkaline phosphatase:alkaline phosphatase immune complexes (APAAP) so that the rabbit anti-mouse IgG acts to bridge the primary monoclonal antibody to the APAAP complex, linking the two together;
(b) treating the tissue of step (a) with a color producing substrate for alkaline phosphatase to visualize the presence of tissue-bound APAAP, and hence tissue-bound antibody to said glucuronide fraction, by incubation of the treated tissue with a color producing substrate for alkaline phosphatase; and
(c) observing the presence and location of color to indicate the presence and severity of the osteopenic pathology.

23. The method of claim 22 wherein the tissue sections are formalin-fixed paraffin-embedded tissue sections.

24. The method of claim 22 wherein the coupling agent utilized is napthol phosphate and the capture agent utilized is Fast Red, to afford a bright red color for indicating the presence of the glucuronide fraction.

25. The method of claim 22 wherein the assay is buffered so as to be kept acidic to protonate said glucuronide fraction, thereby minimizing charge interactions with proteins in tissues and body fluids.

26. The method of claim 21 wherein the alkaline phosphatase-anti-alkaline phosphatase (APAAP) method comprises:
(a) incubating fixed tissue sections mounted on glass slides sequentially with:
1) mouse monoclonal antibody to said 2-hydroxyestrone (2OHE1)-glucuronide fraction; 2) rabbit polyclonal anti-mouse IgG antiserum, and 3) mouse anti-alkaline phosphatase: alkaline phosphatase immune complexes (APAAP) so that the rabbit anti-mouse IgG acts to bridge the primary monoclonal antibody to the APAAP complex, linking the two together;
(b) treating the tissue of step (a) with a color producing substrate for alkaline phosphatase to visualize the presence of tissue-bound APAAP, and hence tissue-bound antibody to said glucuronide fraction, by incubation of the treated tissue with a color producing substrate for alkaline phosphatase; and (c) observing the presence and location of color to indicate the presence and severity of the osteopenic pathology.

27. The method of claim 26 wherein the tissue sections are formalin-fixed paraffin-embedded tissue sections.

28. The method of claim 27 wherein the coupling agent utilized is napthol phosphate and the capture agent utilized is Fast Red, to afford a bright red color for indicating the presence of the glucuronide fraction.

29. The method of claim 27 wherein the assay is buffered so as to be kept acidic to protonate said glucuronide fraction, thereby minimizing charge interactions with proteins in tissues and body fluids.

30. The method of claim 27 wherein said detection can be used to determine progression of the osteopenic pathology and response to therapy.

31. A test kit for the screening of an osteopenic pathology wherein an altered level of a metabolite of estrone and its respective 3-glucuronide is indicative of the pathology or a susceptibility thereto, using the serum, tissue or body fluid medium of a human under test, comprising: (a) a predetermined amount of at least one detectably labeled immunochemically reactive estrone metabolite and its 3-glucoronide, or an antibody binding epitope thereof and; (b) directions for use of said kit.

32. The test kit of claim 31 wherein the labeled immunochemically reactive component comprises antibodies to a 16α-hydroxyestrone (16OHE1)-glucuronide fraction consisting of 16α-hydroxyestrone (16OHE1) and 16α-hydroxyestrone (16OHE1)-3 -glucuronide.

33. The test kit of claim 31 wherein the labeled immunochemically reactive component comprises antibodies to a 2-hydroxyestrone (2OE1)-glucuronide fraction consisting of 2-hydroxyestrone (2OE1) and 2-hydroxyestrone (2OE1)-3-glucuronide.

34. The test kit of claim 31 wherein the labeled immunochemically reactive component comprises antibodies to a 2-methoxyestrone (2MeoE1) glucuronide fraction consisting of 2-methoxyestrone (2MeoE1) and 2-methoxyestrone (2MeoE1)-3-glucuronide.

35. The test kit of claim 31 wherein the label is an enzyme or an enzyme pair.

36. The test kit of claim 35 wherein the label is selected from the group consisting of peroxidase, β-glucuronidase, β-D-glucosidase, β-D-galactosidase, urease, glucose oxidase plus peroxidase, galactose oxidase plus peroxidase, hexokinase plus GPDase, glucose oxidase plus alkaline phosphatase, NAD oxidoreductase plus luciferase, phosphofructokinase plus phosphoenol pyruvate carboxylase, aspartate aminotransferase plus phosphoenol pyruvate decarboxylase, and alkaline phosphatase.

37. The test kit of claim 31 wherein the label is a chemical which fluoresces.

38. The test kit of claim 37 wherein the chemical is selected from the group consisting of fluorescein, rhodamine, and auramine.

39. The test kit of claim 31 wherein the label is a radioactive element.

40. The test kit of claim 39 wherein the radioactive element is selected from the group consisting of 14C, 125I, 131I, 35S, 57Co, 59Fe and 3H.

41. The test kit of claim 31 wherein the labeled immunochemically reactive component comprises the 16α-hydroxyestrone (16OHE1)-glucuronide fraction consisting of 16α-hydroxyestrone (16OHE1) and 16α-hydroxyestrone (16OHE1) glucuronide.

42. The test kit of claim 31 wherein the labeled immunochemically reactive component comprises the 2-hydroxyestrone (2OE1) glucuronide fraction consisting of 2-hydroxyestrone (2OE1) and 2-hydroxyestrone (2OE1)-3-glucuronide.

43. The test kit of claim 31 wherein the labeled immunochemically reactive component comprises the 2-methoxyestrone (2MeoE1)-glucuronide fraction consisting of 2-methoxyestrone (2MeoE1 )and 2-methoxyestrone (2MeoE1)-3 -glucuronide.

44. The method of claim 1 wherein the levels of the particular estrone metabolite and its 3-glucuronide are compared with levels obtained from previous testing of the same subject.

* * * * *